United States Patent [19]
Cox et al.

[11] Patent Number: 5,431,939
[45] Date of Patent: Jul. 11, 1995

[54] HYPERPASTEURIZATION OF FOOD

[75] Inventors: James P. Cox; Jeanne M. Cox; Robert W. Duffy Cox, all of Lynden, Wash.

[73] Assignee: OED, Inc., Lynden, Wash.

[21] Appl. No.: 746,940

[22] Filed: Aug. 19, 1991

Related U.S. Application Data

[63] Continuation-in-part of Ser. No. 674,495, Mar. 25, 1991, Pat. No. 5,283,072, which is a continuation of Ser. No. 349,974, May 8, 1989, abandoned, which is a continuation of Ser. No. 196,878, May 19, 1988, abandoned, which is a continuation of Ser. No. 70,597, Jul. 8, 1987, abandoned, which is a continuation of Ser. No. 758,086, Jun. 24, 1985, abandoned.

[51] Int. Cl.$^6$ .................. A23B 5/01; A23B 5/06; A23B 5/10
[52] U.S. Cl. .................. 426/300; 426/298; 426/301; 426/312; 426/614
[58] Field of Search .............. 426/614, 300, 301, 298, 426/312

[56] References Cited

U.S. PATENT DOCUMENTS

| | | | |
|---|---|---|---|
| 1,888,415 | 11/1932 | Swenson | 426/300 |
| 1,922,143 | 8/1933 | Sharp | 426/300 |
| 2,001,628 | 5/1935 | Nierinck | 426/300 |
| 2,184,063 | 12/1939 | Meyer et al. | 426/300 |
| 2,423,233 | 7/1947 | Funk | 426/300 |
| 2,673,160 | 3/1954 | Feeney | 426/298 |
| 2,758,935 | 8/1956 | Shaffer | 426/614 |
| 3,082,097 | 3/1963 | Haller | 426/614 |
| 3,144,342 | 8/1964 | Collier et al. | 426/301 |
| 3,148,649 | 9/1964 | Moore et al. | 426/300 |
| 3,364,037 | 1/1968 | Mink et al. | 426/614 |
| 3,522,061 | 7/1970 | Whiteford | 426/614 |
| 3,658,558 | 4/1972 | Rogers et al. | 426/614 |
| 4,808,425 | 2/1989 | Swartzel et al. | 426/614 |
| 4,957,759 | 9/1990 | Swartzel et al. | 426/614 |

Primary Examiner—Donald E. Czaja
Assistant Examiner—Mary S. Mims
Attorney, Agent, or Firm—Hughes, Multer & Schacht

[57] ABSTRACT

Methods of treating liquid, semiliquid and solid foods to make them safer to eat and/or to improve the keeping quality of the product. Among the steps that can be employed are: the use of a biocidally active form of oxygen to reduce the population of indigenous microbes, the removal from the food of indigenous gases which may cause spoilage, the replacement of gases removed from the product with gases which are chemically inert or biologically sterile or both, and the aseptic packaging of the treated product. The selected process steps are carried out for a time and at a temperature sufficient to facilitate production of substantially more natural and safer foods than can be obtained if traditional methods of pasteurization are employed.

51 Claims, 14 Drawing Sheets

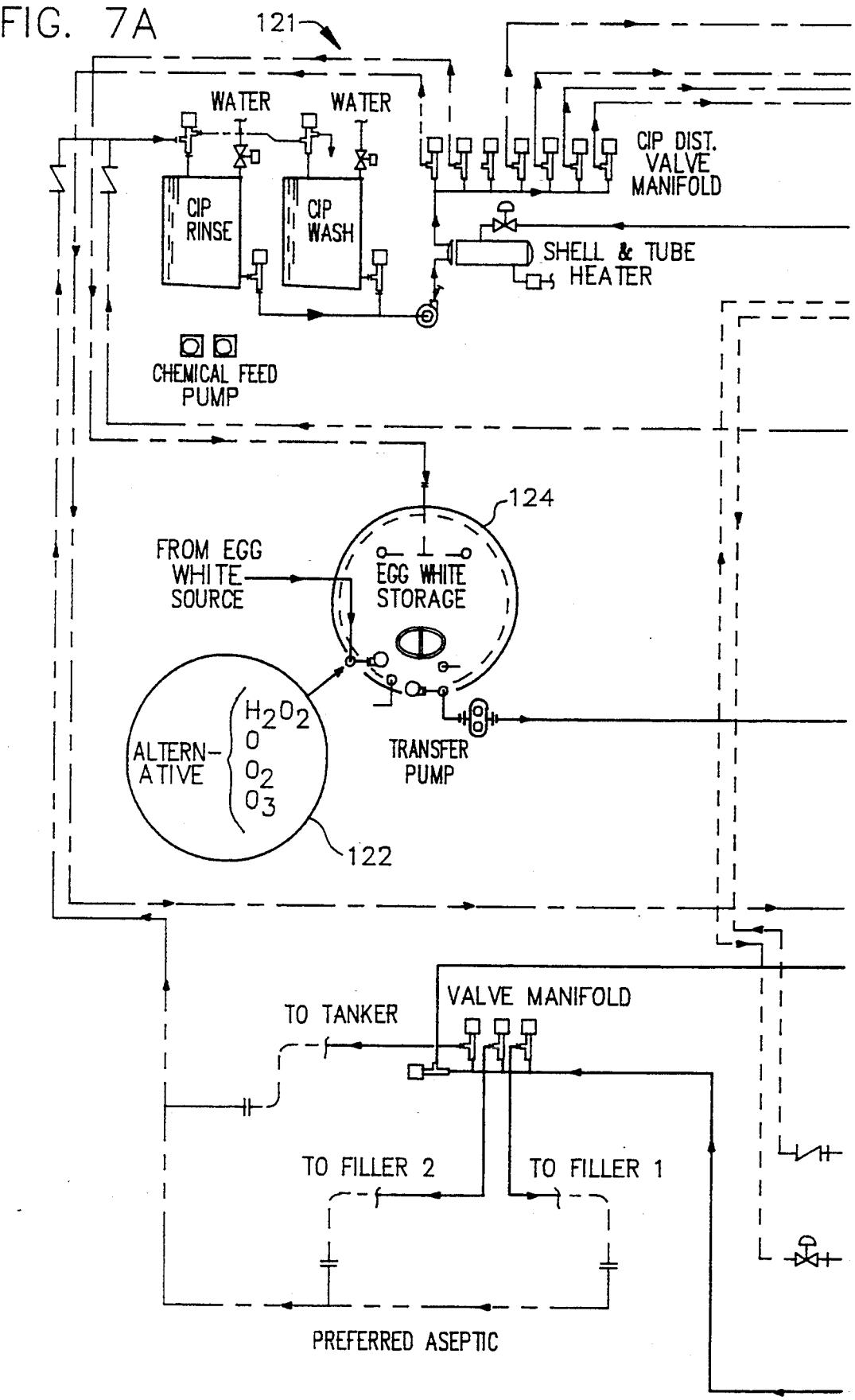

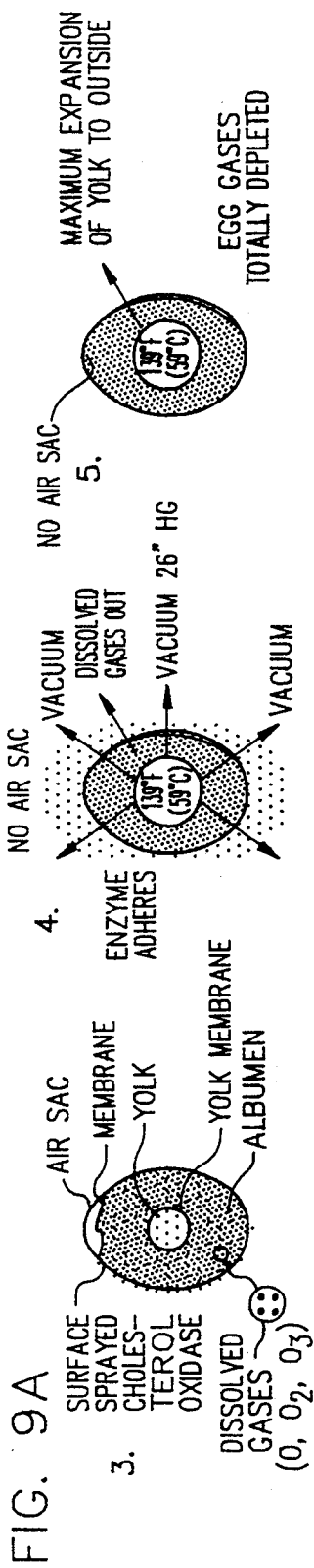

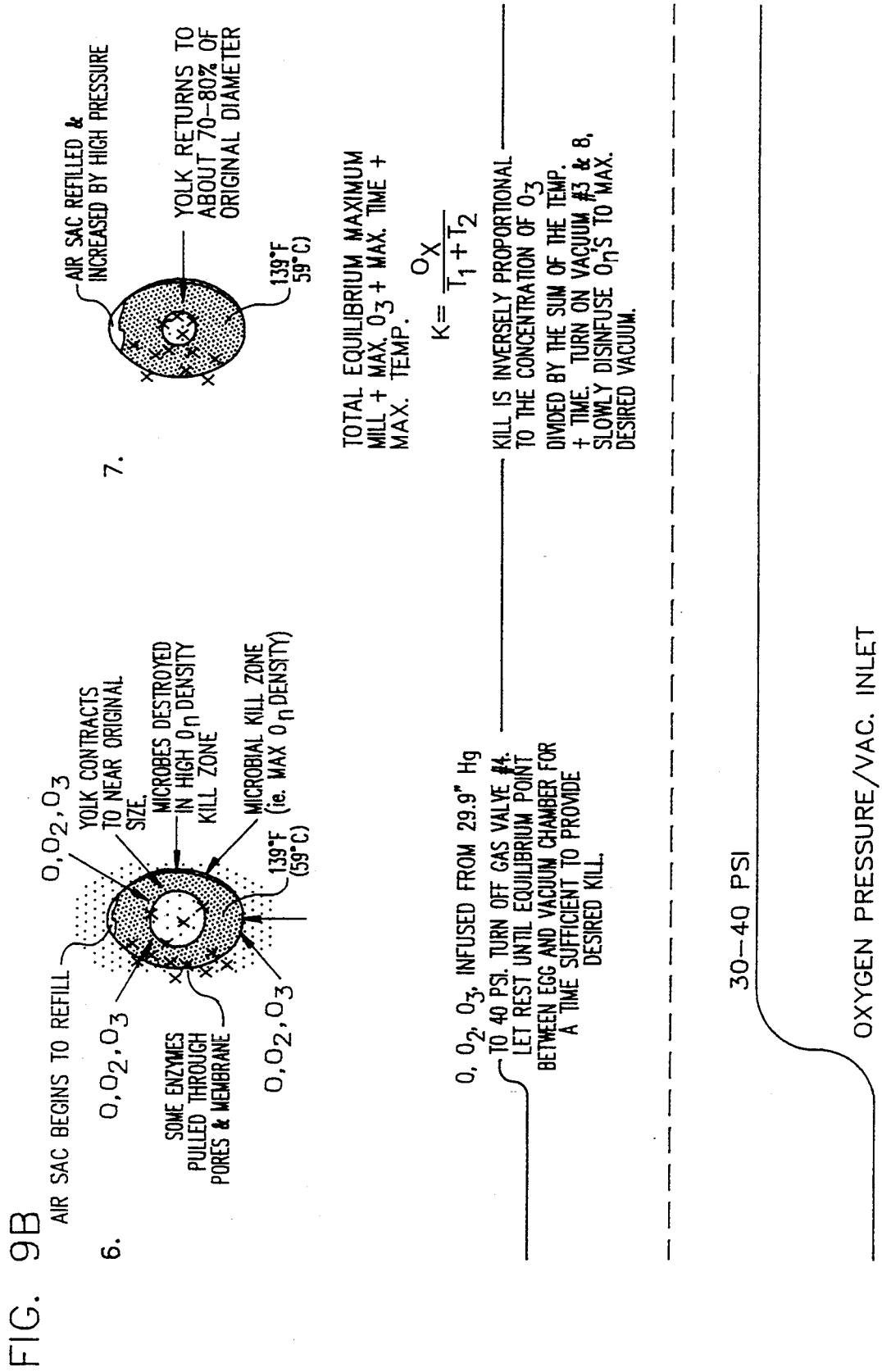

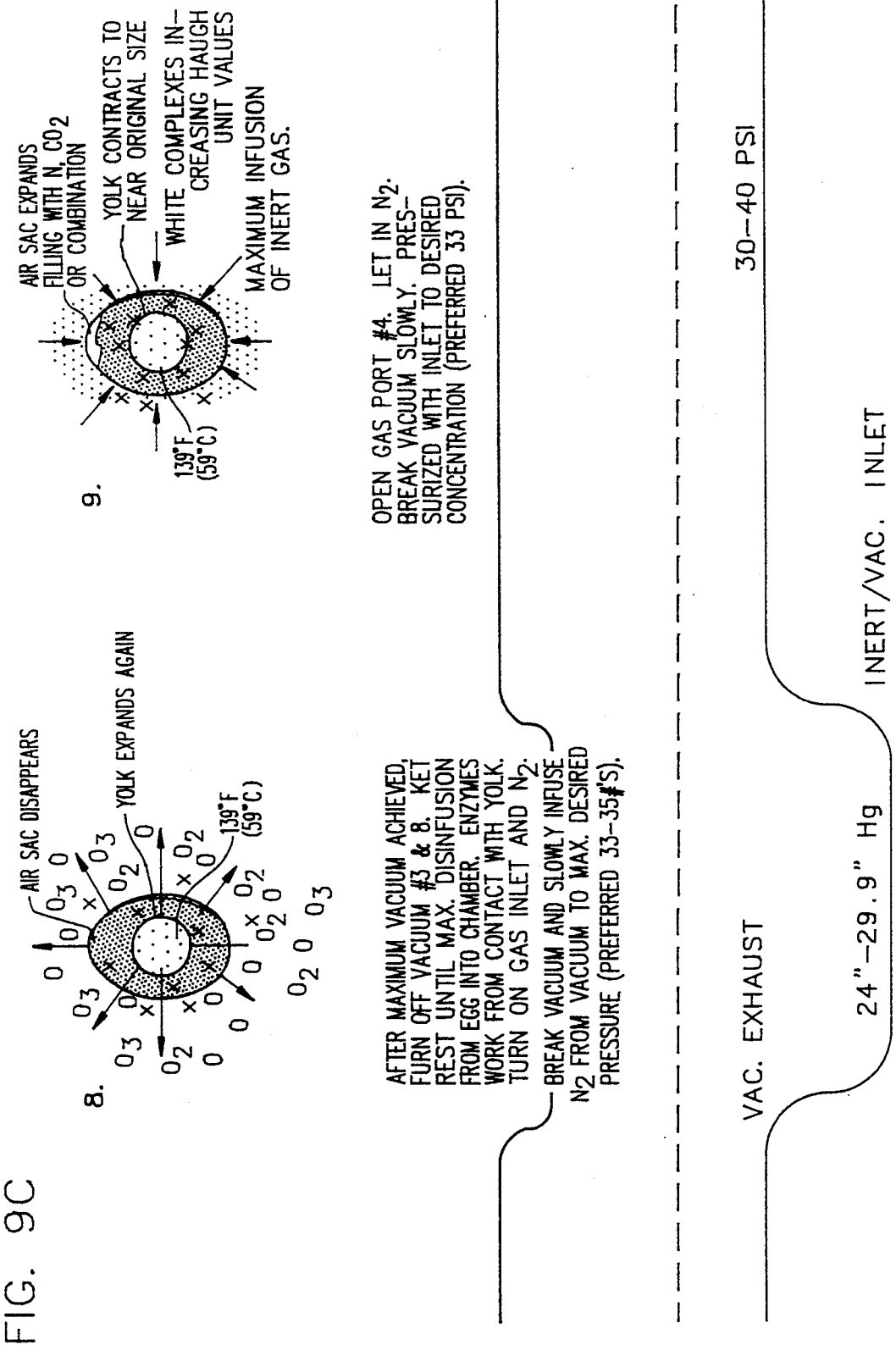

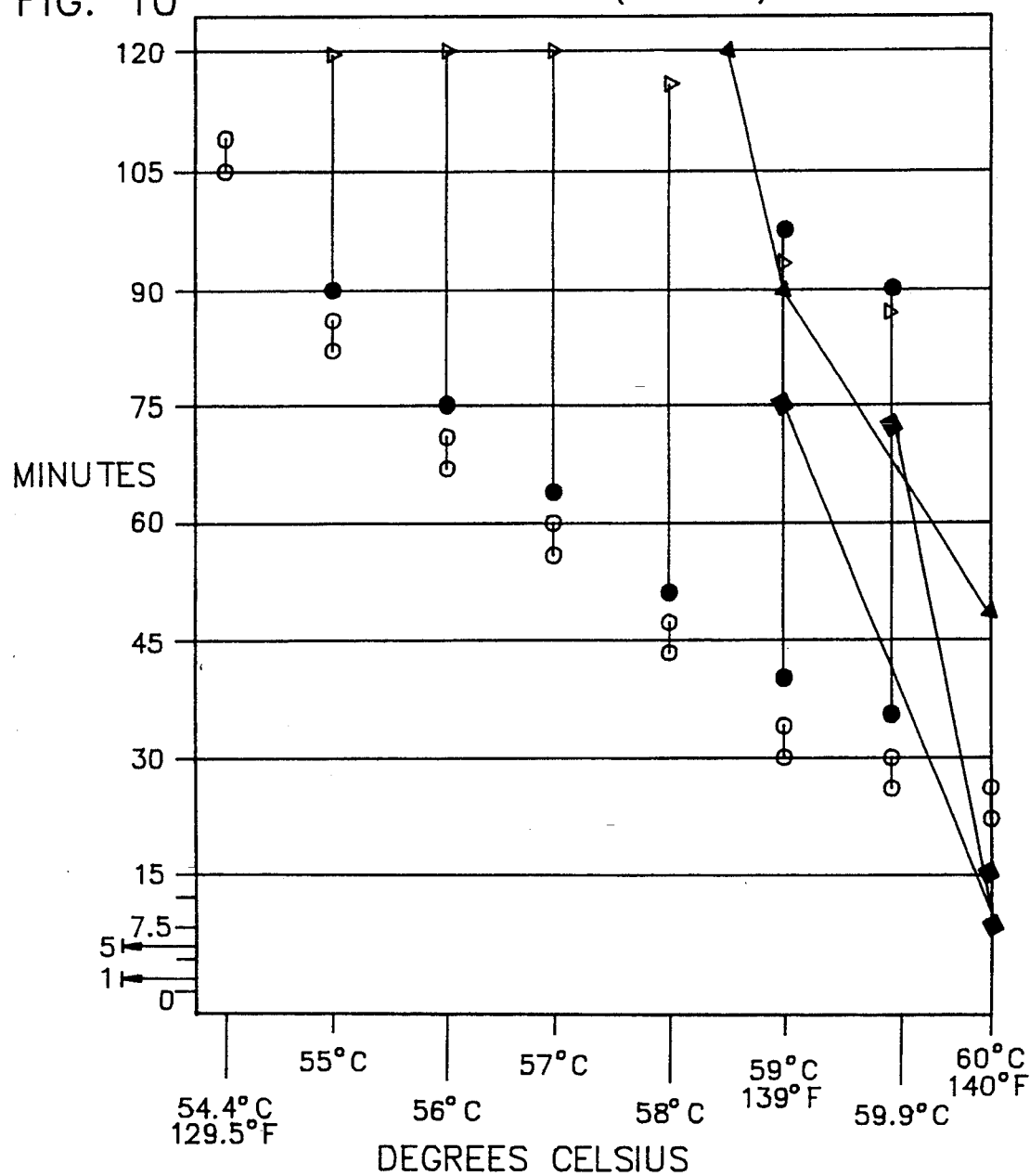

HYPERPASTEURIZATION OF FOOD

CROSS REFERENCE TO RELATED APPLICATIONS

This application is a continuation-in-part of U.S. application Ser. No. 674,495, filed Mar. 25, 1991, now U.S. Pat. No. 5,283,072 herewith, which was a continuation of U.S. application Ser. No. 349,974, filed May 8, 1989, herewith, now abandoned, which was a continuation of U.S. application Ser. No. 196,878, filed on May 19, 1988, and abandoned, which was a continuation of U.S. application Ser. No. 070,597, filed on Jul. 8, 1987, and abandoned, which was a continuation of U.S. application Ser. No. 758,086, filed on Jun. 24, 1985, and abandoned.

DETAILED DESCRIPTION OF THE INVENTION

The present invention relates to methods for producing natural, safer, more stable liquid, semi-liquid and high moisture bearing food products by hyperpasteurization (HP), in particular shell eggs, liquid egg products, red meats and red meat products, poultry meat and poultry meat products, doughs, frozen entrees, milk and milk products, fish and fish products, juices, fruits and vegetables, sauces, salad dressings, mayonnaise, and the like, all of which may be improved in functional and organoleptic properties afforded improved safety as foods and given extended shelf life by hyperpasteurization.

DEFINITIONS

PASTEURIZATION: the process of destroying most disease-producing microorganisms and limiting fermentation in milk, beer, and other liquids by partial or complete sterilization.

HYPER-: over, above, or in great amount.

BACKGROUND OF THE INVENTION

Modern times have seen radical changes in traditional values of many cultures. Nowhere have these changes been more profound than in the United States, none more far ranging than those changes related to food preferences, and no particular food more adversely affected than the poultry egg.

To some extent, this remarkable alteration in cultural food preferences is a result of the fabulous selection and variety of new and alternative food products. To a greater extent, perhaps, it has also resulted from underlying pressure on food systems by dense and increasing populations and competition for traditional foods derived from the land and sea.

Above all reasons, the most dynamic has been the healthy life style phenomenon-an icon of eclectic health preferences constituting passionate advocation to spurious recipes for health and longevity based on food selection and exercise. This movement, almost certainly of future historical note, if not derision, may be characterized as both shallow and over simplified. Issues of extreme technical complexity, both positive and negative, entirely beyond the kin of those attempting to respond to them or journalistically pontificating them, have resulted in tidal movements of consumers towards some foods and away from others.

On the other hand, all of this has served as an iambic to distill a number of issues of inescapable importance into focus. Of vast importance to the vitality of our culture, these issues center on an increasing concern about traditional foods as they relate to food safety, raising questions regarding healthfulness versus. safety values of many traditional foods, including adequacy of methods for processing them.

Regulatory agencies have grown in both scope and focus in light of ever increasing public awareness and journalistic inquisition. Expanding to meet their mandates, authorities have brought a new degree of intensity and sophistication to bear in questioning and then setting new bench marks of judgement about traditional food safety values.

Statistics summarizing egg consumption have shown an increasing decline since the famous (or infamous) Framingham study. This decline in consumption is attributed primarily and almost solely to the cholesterol content of a typical egg.

Increasingly, journalistic reports concerning the food safety of eggs have illuminated the issue of transovarian infection of the egg as it is formed. For reasons not entirely clear, diseased hens excrete microorganisms inside the egg. The microorganism in question is *Salmonella enteritis* (*S. enteritis*).

Salmonella (S.) are small, gram negative, non-sporing rods that are indistinguishable from *Escherichia coli* (*E. coli*) under the microscope or on ordinary nutrient media. All species and strains are currently presumed to be pathogenic for man. As a disease organism, Salmonella produces a variety of illnesses depending on species. *S. typhimurium*, which translates to Salmonella from Typhus Mary, needs no other explanation. *S. typhi* causes a classic example of an enteric fever. *S. paratyphi* type A and type B cause a syndrome which is similar to but milder than typhus. Over 2,000 species of Salmonella are known. The number increases yearly. Reported cases of severe gastroenteritis (stomach flue) have implicated *S. bareilly*, *S. newport* and *S. pullorum* as well. While the mortality range is primarily based on the victim's age and general health category, *S. choleraesuis* has the highest reported mortality rate at 21%.

*S. senftenberg* is reputedly the most heat resistant Salmonella known. It is reportedly destroyed at 130° F. (54.4° C.) after 2.5 minutes. It is estimated that *S. senftenberg* 775W is 30 times more heat resistant than *S. typhimurium*. Turkeys inoculated with 115,000,000 microorganisms (10 to 11 lb. turkeys) kept at an average internal temperature of 160° F. (71.1° C.) required 4 hours and 55 minutes before the bacteria were destroyed.

The most common food vehicles for food poisoning caused by Salmonella are beef, turkey, eggs, egg products and milk. It is estimated that over 40% of food borne disease outbreaks may be traced to turkey and chicken. Studies of chicken from a typical grocery food counter have shown over one third to test positive for Salmonella *S. typhimurium*, the most common form found in the U.S.

Over 538 cases of salmonellosis were reported in the U.S. for dairy products—cheddar cheese, raw milk and certified raw milk. Sausages, particularly pork, bacon, frankfurters, bologna and related meat products are subject to similar microbial problems.

Widespread publicity on sickness and deaths from eggs containing *S. enteritis* in Europe over the past few years has reportedly resulted in a reduction in egg consumption estimated to be as great as 50%.

The problem in Europe and the U.S. is being perceived as chronic, spreading and a major challenge in public health.

Nevertheless, even with the U.S. reduction in consumption attributed to public concerns over cholesterol, approximately 240,000,000 dozen eggs are consumed annually.

Reports by the Center for Disease Control (CDC) have traced development of food poisoning incidents in the U.S. In 1991 there were reported to be 76 cases of regional food poisoning outbreaks resulting in 17 known deaths ascribed to *S. enteritis.*

The USDA has increased monitoring of poultry flocks. Eleven major flocks have been found to be diseased with Salmonella type E. So far, the incidence of disease seems to be more or less isolated to the northeastern states. However, reports of *S. enteritis* have been reported as far away as Washington and California. In 1991, there have to date been 104 reports from Washington state and over 400 from California.

A recent article in Nutrition Action Health Letter published by the Center for Science in the Public Interest, July/August 1991 edition, Volume 18, number 6, "NAME YOUR (FOOD) POISON," relates a current trend of growing concern. The article reports that, according to government estimates, 80,000,000 cases of food poisoning yearly result in about 9,000 deaths and several billions of dollars in health costs.

The article claims that the primary causative foods are, in order: dairy products, eggs, poultry, red meat and seafood.

In 1985, 47 people died in southern California from eating raw milk cheese. In 1985, tainted pasteurized milk caused 16,0000 confirmed cases of Salmonella food poisoning in Chicago. Health authorities estimated that 200,000 people may have been affected.

The following quotes from federal USDA inspectors appeared in the article:

"Would you want to go out to a pasture with a chicken, cut him up, then drop him into a fresh manure pile and eat him? That's what the product is like coming from chicken plants today."

"Practically every bird now, no matter how bad, is salvaged."

"I've had bad air sac birds that had yellow pus coming out of their insides, and I was told to save the breast meat off them . . . You might get those breasts at a store in a package of breast fillets."

"I would never, in my wildest dreams, buy cut up parts at a store today."

The article continues " . . . Even the USDA admits that as much as a third of all chicken sold in supermarkets is contaminated. Some surveys put the figure as high as 90 percent . . . "

With respect to consumers who want to continue to use poultry, the article suggests the following:

Always buy the poultry last at the supermarket.

If it will be more than two hours before you are able to refrigerate the chicken, carry an ice chest in your car.

Washing raw poultry may actually help spread bacteria rather than reduce contamination of the surfaces.

Was everything that comes in contact with the poultry with hot water and soap-hands, knife, cutting board, counter, sink—everything.

Remove the skin. Machines at the processing plant which de-feather chickens often pound dirt and feces into the skin pores. Cook the poultry until the juices run clear, i.e., 180° to 185° F. in the thickest part of the meat.

With respect to eggs, the article reports that 1 in 10,000 eggs is contaminated with Salmonella. The average American consumes about 200 eggs per year. Your chances of downing a contaminated egg are 1 in 50.

If you are over 65 or have a disease such as cancer or AIDS associated with a weakened immune system, the article advises: don't eat raw eggs, don't drink egg nog, don't eat Caesar salads, home made mayonnaise or ice cream, or "health" drinks that call for raw egg. Cook eggs thoroughly—solid white and yolk.

With respect to red meat, the article reveals that health food authorities are tracking a "nasty" bacterium, *E. coli* O157:H7, which has caused food poisoning from raw and under cooked beef, including "precooked" ground beef patties served in restaurants, hotels, schools, and nursing homes. The beef had not been precooked enough to kill the bacteria which is thought to be the leading cause of acute kidney failure in children.

The article continues with respect to fish and shellfish, asserting that these are among the very worst offenders. It ended up suggesting that, if you are over 65 or have a weakened immune system: do not eat raw shellfish, be selective about where you eat fish, and "over" cook any fish or fish products within 24 hours of purchase.

If the foregoing were not bad enough, what future findings will be likely with greater scrutiny of food safety using today's technological capabilities and knowledge base? The current focus is clearly on the obvious microbial troublemakers, but what about others less obvious? What about parasites? Viruses?

If the egg industry cannot answer the immediate challenge and be in a position to deal with future ones, eggs may well disappear from the American diet. This is also true of milk, meat, poultry, fish and many other foods which have as yet not seen the kind of challenge that has been posed to the egg industry over the past few years.

Alarmed by the reports of egg contamination, institutions have began to require liability insurance from egg suppliers. In turn, fierce competition from remaining markets has narrowed profit margins to a point where egg producers cannot profit and comply.

Egg producers point out that it is improper handling itself by the institution which is most responsible for the problem. They cite the eggs all too often seen setting out at room temperature for long periods of time in institutional kitchens, promoting bacterial advancement in even the freshest egg.

The problem is by no means confined to eggs. Increasing incidents of food poisoning and concerns by health officials extend to milk, milk products, cheeses, sausages, fresh meat and many other foods. For example, it is currently being recommended that poultry be cooked "until the meat falls from the bone."

It is also currently believed by many in the food industry, including those in the meat, poultry and egg fields, that ionizing radiation can be utilized to provide safe to eat shell eggs and other foods.

Salmonella is amenable to treatment by ionizing radiation. Doses of no more than 0.5 to 0.75 millirads are sufficient to eliminate salmonella bacteria from most foods and animal feeds. Reported values for treating a variety of products are on the order of 0.5 millirads to destroy $10^7$ *S. typhimurium* in frozen Whole egg, while 0.65 millirad was required to give a $10^5$ reduction in bacterial count in frozen horse meat. 0.45 millirad was required to give a $10^3$ reduction to bone meal.

However, radiation treatment must be clearly marked on the package according to current FDA statutes, causing a distinct marketing problem. Also, ionizing radiation treatment of shell eggs and other foods at sufficient levels to provide food safety will result in the formation of free radicals, including peroxides. Trapped inside the foodstuff, peroxides alter the natural flavor of the food, causing it to spoil faster due to the formation of free fatty acids and other breakdown products.

Thus, while microbial kill can be facilitated by radiation, the residue peroxides, even in trace amounts, attack lipids and other food components to an extent leading to spoilage from oxidative rancidity. In most cases, the alteration of characteristic sensory aspects resulting from these resides of the food are noticeable immediately after treatment.

Treatment by ionizing radiation is expensive, requiring skilled operators and maintenance staff.

The overall disadvantages mentioned may prove to be sufficient impediments to bar the use of ionizing radiation to provide safe shell eggs for consumer consumption.

While Salmonelias are amenable to irradiation, what about the bewildering host of other common and not so common microbes; *Escherichia coliform* or complete genera such as Pseudomonas, Streptococcus, Acinetobacter, Proteus, Aeromonas, Alcaligenes, Micrococcus, Serratia, Enterobacter, Flavobacterium and Staphylococcus, to mention a few?

Just as foods all contain some percentage of water of hydration, all foods contain some percentage of dissolved gases. In dry foods such as cereals, the amount of indigenous dissolved gas is small. In wet foods (those containing more that 50% water), however, the percentage of indigenous dissolved gases is significant.

When a liquid such as tap water or the liquid in whole eggs is subjected to a substantial vacuum, it soon begins to boil as the dissolved gases expand and rise to the surface. Heating the product facilitates and speeds up the gas disincorporation process due to concomitant expansion of gas.

The make-up of the gases may be related to the particular food, whether it respires, is viable or not, and whether or not there are symbiotic or indigenous microbial populations associated with the food. The type and concentration of indigenous gas in a food can also be the best indication of the food's condition and safety since the gas complexes change in accord with the chemical processes taking place within the food.

The gases are stored by condensation, Van der Waal's attraction and entrapment within the natural interstices of food. The food type, basic chemistry, pH, condition, percentage of moisture and other factors influence the type and percentage of indigenous gases.

Foods in their natural condition contain different concentrations and types of gas than processed versions of the same foods. Processing sometimes results in substantial additional gas concentrations and can alter significantly the type of gas complex in a food.

The results are sometimes desirable and other times are destructive to overall food safety and keeping quality.

In many instances, a significant portion of the interstitial gases is ambient air. In others, entirely different complexes may be the result of internally generated gas complexes. In food systems which contain any significant degree of oxygen, the potential and type of microbial growth will be influenced as will the ability of basic components of the food to stand up to oxidative processes.

Even small percentages of oxygen ($O_2$) molecules will, over time, take part in some oxidative breakdown of the food or act as a force in determining aerobic or anaerobic microbial growth. Sometimes referred to as "oxygen tension," this factor is a significant one in defining the characteristics of food safety and keeping quality.

Nowhere is oxygen tension more important than in the lipid portions of foods. The double bonds of lipids are particularly vulnerable to the presence of oxygen, even in minute amounts. The most common result of oxidative rancidity results in the formation of short chain fatty acids. Not only do short chain fatty acids have pronounced and usually unpleasant odors, but many are toxic. Traditional pasteurization, a common food processing technique, addresses only microbial spoilage, sometimes at the expense of promoting premature oxidative spoilage by altering the composition of the gases in the food being processed.

Ozone ($O_3$) in small concentrations has been employed during cold storage to preserve some foods, such as eggs. The presence of ozone in cold storage air is effective in preventing growth of microbes, including fungus and molds. Foods dipped in ozone impregnated water have been proposed. In these applications, control of microbial spoilage is external to the food product and influences food surfaces, destruction of airborne microbes and microbial spores.

High ozone generating ultraviolet lamps have been used for the same reason by some food industries. Cheese and dairy manufacturing operations frequently employ "germicidal" lamps in packaging and food processing areas to reduce airborne microbes.

Of course, it is the ozone generated by these lamps which assists in controlling airborne microbial contaminates. This, in turn, reduces exposure of the food to potential spoilage organisms.

Ozone is recognized as a sterilant par excellence, particularly for producing potable drinking water. Outside of limited applications for deodorizing food cold storage rooms and retarding some surface growths, it is not, however, been believed applicable to food for preservation.

This belief is based on assertions that ozone has very poor penetrating qualities and is therefore of limited value in treating foods. Also, ozone imparts a characteristic odor to food. And the presence of ozone enhances and accelerates oxidative rancidity.

There are some indications that ozone ($O_3$) somehow catalyzes or mediates oxygen ($O_2$) and that it is the oxygen ($O_2$) which, as matter of fact, demonstrates the primary sterilizing quality.

Nascent oxygen (O) has only a brief half life. While thought to be of importance in sterilization, however, it only plays a role when products are exposed directly to ultraviolet radiation when nascent oxygen is formed on the surface.

A somewhat related technique, employing hydrogen peroxide in conjunction with peroxidases, has proven effective for reducing microbes in milk and liquid egg replacers.

U.S. Pat. No. 4,808,425, Swartzel et. al, summarizes many other references and resources relative to egg pasteurization and adequately points out many of the problems associated therewith.

Liquid whole egg treated with the Swartzel et al. ultrapasteurization process has been produced and distributed, meeting with good commercial success for the reasons anticipated by the inventors. Yet, commercial products produced by the Swartzel et al. process have not adequately resolved many problems attendant with the antecedent products mentioned therein. Off flavors, reduced functionality and general problems related to balancing their ultrapasteurization treatment against organoleptic degradation of eggs has led: to a failure to meet product claims, to customer dissatisfaction and to increased scrutiny of finished products by authorities.

Swartzel et al. do advance the utilization of liquid whole egg products in the right direction. However, as a practical matter, the invention runs into the many limitations attendant with trying to match time and temperature to produce a product which is not decharacterized and is still safe.

Ultrapasteurization as taught by Swartzel et al. is clearly an attempt to ultra-optimize traditional pasteurization, thereby producing egg products which can meet the challenge of a technologically sophisticated and demanding consumer. Swartzel et al. marks a point at which the limits of traditional pasteurization process technology is no longer applicable, a point at which the ultimate limit of the original technology can no longer be utilized effectively.

Swartzel et al. can treat only liquid egg products; this is done by contacting them against a heated surface at high temperatures, i.e., 140° F. (60° C.) for short durations, i.e., less than 10 minutes.

This is not possible with a shell egg. If the outer shell is contacted with a heated surface at the lowest temperature proposed by Swartzel et al., 140° F. (60° C.), the membrane inside the egg would begin to cook while the immediately adjacent albumen would coagulate in layers radiating inwardly. In effect, each layer would act as an insulating barrier for heat transfer; and long before any significant inner portion of the shell egg could reach 140° F. (60° C.), the outer portions would be cooked. Thus the Swartzel et al. process applied to shell egg would simply cook some portion, leaving some portion untreated, or substantially cook all portions.

With liquid whole eggs, the results of applying Swartzel et al. are that the functional and other important aspects of the egg, including organoleptics, baking quality and syneresis after cooking, are radically changed from normal in ways quite obvious to consumers.

Other workers have also stopped short or somehow overlooked important time and temperature conditions which can achieve desired goals in egg technology-maximum safety with minimum changes in the natural product.

For example, the heretofore proposed thermostabilization technique is a method of preserving shell eggs by briefly heating the egg, i.e., 15 minutes at 130°-135.9° F. (54.4°-57.7° C.). It cannot possibly provide a Salmonella free or Salmonella reduced inner egg product. Temperatures at the egg center never achieve 130° F. (54.4° C.), the minimum temperature-needed at 2.5 minutes to kill Salmonella bacteria.

In short, current, state-of-the-art processes for pasteurizing eggs and egg products aim at egg/microbe contact with a critically hot surface for a time sufficient to reduce microbial populations. In the case of whole shell eggs, these prior art processes merely treats the surface layers of a shell egg which is ineffective to destroy microorganisms inside the shell. Also, current USDA guidelines call for the treatment of a whole egg at 140° F. (60° C.) for 3.5 minutes. Such treatment results in irreversible alterations in functionality of shell eggs so processed.

Other workers have approached the problem in the same way. While the temperatures recommended by them vary widely, as do the times, it is clear that none of the time/temperature combinations allow the egg to achieve adequate temperature for enough time to even reduce microbes at or near the center of shell eggs, let alone reach those temperatures there for long enough to substantially destroy microbes of the Salmonella type. It is known, for example, that $S.$ $senftenberg$ requires exposure of at least 130° F. (54.4° C.) for no less than 2.5 minutes. Even the USDA guidelines will not provide a shell egg that would be significantly reduced in Salmonella beyond the immediate inner shell surfaces.

Others have proposed oiling or otherwise surface treating eggs to influence vapor and gas diffusion through the shell. And, at least one method involves cooking or setting the inside albumen into an inner cooked layer as an oiling alternative. None of these processes have met with any significant approval. Nor is it expected that they would.

Improvements to traditional pasteurization techniques have been manifested over the years to obtain important but increasingly modest gains in food safety. However, pasteurization has always been, and still is, limited in that it addresses only one aspect of food safety—control of microbial populations. As discussed above, however, there is another aspect of spoilage just as important—oxidative changes including those resulting in oxidative rancidity. Oxidative damage would be expected to occur in the lipid portion, of a food. However, it has been found that oxidative degradation occurs in carbohydrates, non-lipid volatiles and protein fractions as well.

To a great extent, it is for this reason that atomic or nascent oxygen (O), molecular oxygen ($O_2$) and ozone ($O_3$) are universally considered undesirable for use in food preservation with few exceptions.

Some exceptions are where the food value is increased due to accelerated oxidation, such as with some vinegars. This application takes advantage of ozone's known disadvantage when added to food—the production of flavors, odors, textures and tastes associated with accelerated aging or what is usually considered spoilage in fresh foods.

One problem left unanswered by prior art, of course, is that of insuring that not only those microbes on the surface of a shell egg, but those inside, outside and sometimes throughout, including even the most intimate parts of the yolk, are destroyed. While this form of contamination is thought to be far less frequent, it is nevertheless of great concern with respect to food safety. Excreted by the hen at the time the egg is formed, this type of microbial infection is referred to as transovarian infection. Eggs infected in this way are not in the least amenable to control by any known method heretofore proposed. The microbe most commonly known to be involved is $S.$ $enteritis.$ Little is known about virology inside the egg. Many believe shell eggs to be sterile inside the shell. Needle puncture samples of the inside of an egg including both yolk and white taken under aseptic conditions usually do demonstrate a negative plate count when cultured. Nevertheless, it is well known that, when eggs are broken in quantity, they immediately demonstrate significant gross populations of microbes. It is not unusual to find plate counts ranging from several hundred to many thousands, even when the surface of the egg shells have been cleaned of filth and washed in the best antiseptics known to food science. The occurrence of *S. enteritis* inside the shell egg, for example, is well documented.

The problem is that egg shells have pores which permit the egg to breathe. Pore holes vary in size, some being larger or damaged. If, when the egg is laid, those holes come into contact with organic refuse in the cage, some microbes contacted are of a size that can fit through those large pores.

Such entry pores only occur randomly on an egg shell surface. Once inside, the microbes are not spread around the interior consistently but are retained in small patches on the inner shell membrane which has yet smaller pores than the shell.

Washing actually spreads microbes more evenly, increasing contamination through greater surface contact with entry pores. When the eggs are cracked, the membrane may be ripped and torn loose, of course. And, when emptied, the eggs may be peppered with this stored innoculum in addition to airborne bacteria.

In addition, there is, of course, active and ongoing gas and vapor exchange between the yolk and white via the vitelline membrane, between the white and the inside of the shell via the outer and inner shell membranes and also between the shell and the outside environment. These processes can also result in microbial contamination that is not reached by known sterilization techniques.

Numerous methods have been suggested interfering with part of this transpiration by plugging shell pores, usually at the outer shell surface. None of these proposed solutions appear to have been found satisfactory.

SUMMARY OF THE INVENTION

The above-discussed and other drawbacks and disadvantages of heretofore proposed techniques for reducing the bacterial populations of foods are eliminated, in accord with the principles of the present invention, by employing a process referred to herein as hyperpasteurization. This process, which also has the advantage of keeping the treated foods fresher for longer periods of time, and in a more natural state, differs from the pasteurization processes known to the art in several important respects.

Hyperpasteurization, as one example, refutes the conventional wisdom that nascent oxygen (O), oxygen ($O_2$), and ozone ($O_3$) are undesirable for use in food preservation with those few exceptions discussed above.

The major factor overlooked in the assessment of the powerful advantages of nascent oxygen (O), oxygen ($O_2$) and ozone ($O_3$) placed inside a food as a potentially important step in preservation has been based on the failure to understand that, under controlled conditions and in appropriate concentrations, selected active oxygen species can be used to destroy any or all microbes, then removed, reacted and/or replaced to interrupt or prevent significant or noticeable reactions, whether immediate or ongoing, with non-viable portions of the food so treated. Hyperpasteurization takes advantage of the microbiocidal phenomenon just described to destroy bacteria in a manner which results in the treated food retaining its desirable natural properties.

The microbial effect of the active oxygen is to selectively destroy particular viable microorganisms, usually anaerobes first, then aerobes and, finally, spores thereof. Selection of the oxygen(s), ratios and concentrations provide desired levels up to complete levels of microbial sterility. Additions of oxygen and other conditions can be so made that any food component destruction is minimal. Removal from food interstices of all possible oxygen species, including those in indigenous dissolved gases, may be required in most cases. Providing inert gases to food interstices at other than ambient pressure equilibrium can provide vastly increased stability against oxidative processes common to both untreated and/or oxygenated food. Packaging is important. In most cases aseptic packaging is the preferred form.

Selection of the best process parameters for any specific food, the treatment steps, amounts of treating agents, temperatures, times, proper sequencing and overall conditions needed to obtain the desired level of microbial and oxidative food safety improvement to improve or retain equivalency may be readily and empirically established for each food by anyone skilled in the arts to which the present invention relates.

In short, the use of concentrated forms of oxygen under the right conditions can not only be used to microbially improve or sterilize many foods without causing expected off flavors, tastes or oxidative rancidity, but can also actually prevent or retard those forms of spoilage which would otherwise occur naturally in the untreated food while still providing a substantially equivalent or even improved processed food as compared to unprocessed.

The basic essential elements of a more pronounced treatment to provide for elimination of all microbial contamination including high initial and thermal resistant concentrations may be provided, still with hyperpasteurization, by utilizing the just-discussed infusion of microbially destructive concentrations of selected oxygen species (O, $O_2$ and $O_3$) onto and into food interstices at a temperature and for a time sufficient to reduce or sterilize microbial populations thereof, in combination with disinfusion and/or displacement of substantially all residual selected oxygen.

Also, when applied to high moisture foods, including shell eggs, the contact treatment with oxygen may be improved by vibrating or shaking the food being treated during addition of the oxygen. Vibrations may be in the ultrasound range which can measurably enhance not only gas/food contact and, in some cases, generate or co-generate desirable high pressure oxygen domains.

When the food being processed is a liquid, agitation during the infusion and maximum concentration periods of selected oxygen can also enhance and shorten process times. High speed agitation can be used to augment hypobaric-hyperbaric applications by achieving cavitation velocities across turbulent mixing surfaces such as at high shear mixing blade surfaces. Cavitation points can increase intimacy of contact between the oxygen and food particles, thereby enhancing the speed and effectiveness of treatment.

Useful oxygen sources are air and purified air in combination with supplemental nascent oxygen (O), oxygen ($O_2$) or ozone ($O_3$), blends or pure oxygen, or allotropic forms thereof including peroxide (—O—O—). The oxygen may be bottled, liquid or generated at time of use as by ultraviolet silent arc, and by adding and reacting loosely associated forms such as those resulting from the breakdown of hydrogen peroxide ($H_2O_2$) and like compounds.

The effectiveness of hyperpasteurization is substantially enhanced when the foregoing steps are carried out under either hyperbaric or hypobaric conditions. Effectiveness is maximized when hyperbaric and hypobaric conditions are alternated during processing. Oxygen scavengers such as iron and glucose oxidase may also be used effectively.

After treating the product with oxygen and subsequently dearating it, precautions can be taken in subsequent processing steps to insure that ambient air is not reincorporated at any point. This can be accomplished by entraining an inert gas or combination of inert gases in the product, thereby supplying the deaerated product with inert gas upon restoration of atmospheric equilibrium. Inert gases are particularly useful for reducing the tendency of the product to spoil or support microbial growth.

The inert gases used may be selected from those commonly used in food products. For example, nitrogen ($N_2$) or combinations of nitrogen and carbon dioxide ($CO_2$) may be used. A preferred gas mixture is one containing 75% nitrogen and 25% carbon dioxide.

In addition, and as was just suggested, the keeping quality of the food, once treated, is best maintained by extending the process to infuse either one or a plurality of inert gases into the interstices of the food. In most instances, the treated food is also best aseptically packaged in the selected inert gas(es).

Differing foods may be either easier or more difficult to process, and some may be processed by minimal hyperpasteurization methods. The preferred procedures for high spoilage potential foods (such as whole fresh raw shell eggs, fresh raw liquid eggs, raw and processed poultry meat, whole poultry, ground and whole beef, pork, lamb and other raw and processed meats, liquid foods such as milk, fruit and vegetable juices, beer and wine, semi-liquid foods such as mayonnaise, salad dressings, sauces and such, and even cheeses, doughs and frozen prepared foods such as entrees, pot pies and the like) are carried out in either a liquid filled system or a vacuum chamber. Liquid foods are processed in a liquid system; solids and semi-solids are processed in a vacuum/pressure chamber.

Process economies may require raising the temperature of the food to that maximum possible temperature which will not cause noticeable irrevocable changes in the food, i.e., cook it. With eggs, for example, a preferred temperature is 139° F. (59.4° C.). Oxygenation can be accomplished at ambient temperature, but it requires greater concentrations of oxygen and longer periods of time.

When ozone is generated for immediate use in the food, it can be generated at the time and point of use by passing either oxygen or oxygen with high humidity air over an ultraviolet light, preferably one emitting energy in the 1,800 Å to 2,600 Å range (2,537 Å is preferred).

While little ozone is likely to survive the high pressure/vacuum treatment chamber, particularly at high humidity and temperature, a zeolite (crystalline aluminum silicate) filter can be used to disassociate any residual ozone if this is deemed necessary or appropriate. For example, for a chamber of from 2 to 700 cubic feet, the chamber exhaust can be passed through a filter containing zeolite packed in a zone at least 300 mm. (1 ft.) long and 25 mm. (1 in.) in diameter.

A wide range of ozone concentrations may be used, depending upon the food to be processed and the desired degree of microbicidal effect. Generally, the range can be from about 0.005 ppm, based on the gases in the processing environment, (or even less for extended processing periods) to 50 ppm and more for shorter periods. Preferred ranges for most foods at process temperatures ranging from ambient to about 140° F. (60° C.) is 0.5 ppm to 10.0 ppm based on the total gas in the pressure/vacuum chamber. Preferred concentrations include 1.5 ppm for liquid eggs, about 2.0 ppm for shell eggs, and about 2.25 ppm for poultry and meats.

Preferred for infusion in food interstices is a concentration on the order of 2.0 ppm for a period of about 5 minutes at 139° F. (59.4° C.). This concentration has been shown to be 99.9% to 100% effective against *E. coli*.

Nascent oxygen (O) is very short lived and is employed effectively when the food product is presented to an ultraviolet source at close range. One method employed with liquid foods in particular is to pump the liquid with admixed nascent oxygen through a chamber containing a source emitting electromagnetic energy at 2,537 Å. Some nascent oxygen (O) is converted into oxygen ($O_2$), and ozone ($O_3$) which may then be flushed with saturated oxygen into chamber.

Thus, hyperpasteurization may be employed to adversely impact the microbial status of a given food to make it safer to eat and improve its keeping qualities. In addition or even alternatively, it can provide improved food which will stay natural and fresh longer due to removal and replacement of oxygen by an inert gas within the interstices of the food.

The accomplishment of the first objective has been the goal of traditional pasteurization while the second has been the object of oxygen barriers, antioxidants and packaging.

In conjunction with the foregoing, it will be appreciated that the hyperpasteurization process disclosed herein has the particular advantage, when applied to whole or shell eggs that it interferes with the transpiration—or gas and vapor exchange—processes discussed above.

This ability to intrude on all of these areas of transpiration and, indeed, the substitution of different gases such as air, filtered air, sterilized air, nitrogen ($N_2$), carbon dioxide ($CO_2$), carbon monoxide, oxygen and its allotropes or combinations thereof for existing gases in the transpiration processes can effect surprising results. Examples include improved appearance and freshness, vastly improved microbial safety, improved functionality, reduction or elimination of oxidative potential and improved keeping over extended periods of time.

Finally, there is to be considered oxygen transported in air from outside the shell to the inside and that which is already inherent in the egg as indigenous oxygen. Over time, ambient and interstitial oxygen can contribute to the increase of microbial populations and inexorable oxidative processes, usually at the double bonds of egg lipids. Interference with these processes is also an important and available attribute of the processes disclosed herein.

The process of the present invention may be used to so treat shell eggs, egg products and, many food products including those identified above to produce products which are better, fresher, more natural, even improved, safer and longer keeping than any heretofore practicable.

Thus, hyperpasteurization addresses problems heretofore considered by Swartzel et al. and others—reduction of bacterial populations and prevention of oxidative degradation. However, HP has the advantage that it can be used to treat treatment of many foods instead of one or a small group of foods—for example, the whole liquid whole egg to which the Swartzel et al. process is limited.

Hyperpasteurization provides, for many foods, improved methods of making them safe to eat while retaining a natural or even improved condition not achievable by traditional pasteurization methods. The intimate treatment of food by oxygen applied at other than ambient pressure in one or more of its active forms in conjunction with other specific selected treatments makes possible for the first time the objective of controlling the degree of safety imparted to a wide variety of foods from microbial reductions to sterilization while still retaining or even improving functionality, appearance organoleptics and even retardation of normal oxidative processes.

From the foregoing, it will be apparent to the reader that one realized object of the present invention is to provide an alternative to pasteurization and other heretofore proposed techniques for making foods safer to eat and drink, especially those foods which are marginally or totally unamenable to traditional processes.

An additional object is the provision of methods for making food products which are safe to eat and not abcharacterized by the process from foods which are not amenable to the prior art processes.

A specific objective is to provide a shell egg which is safer to eat and of improved keeping quality.

Another specific objective is to provide poultry which is safer to eat.

A particular object is to provide treated products with chacteristics substantially equivalent to those of untreated products but of improved safety for eating, even when kept over extended periods as measured by current standards for a particular food.

Another particular object is to provide a process which may be accomplished at sufficiently low temperature to preserve the food quality in its natural state while, at the same time, affording an improved degree of food safety with respect to eating and improved keeping quality.

An important object is to provide a process which may yield food products that: are Salmonella free and thus of improved safety as foods, but which, after processing, are of natural or improved quality functionally.

Another object is to provide treated food products which may contain substantially no additives or residues resulting from the treatment.

A further object is to provide food which is safer from spoilage by both microbes or oxidation.

An important object is to provide safe food preserved in as natural a state as possible.

Another object is to provide a process for improving safety and storage of food which does not adversely influence keeping quality.

A further object is to provide a method of improving the appearance of freshness of treated food, including shell eggs.

An important object is to provide a method of improving the safety of food which may be economically applied to a range of foods.

Another object is to provide a natural process for improving the safety of foods which does not create concern over long term adverse health effects.

An important object is to provide a process which may be employed for the improved safety and keeping of animal feeds.

An object is to provide a process for improving food safety while preserving substantial nutritional equivalency of foods when processed by use of traditional processes.

Another object is to provide a versatile process treatment which is sufficiently flexible to be used to provide a wide range of food safety improvements.

Still other important objects, features, and advantages of the invention will be apparent to the reader from the foregoing and the appended claims and as the ensuring detailed description and discussion proceeds in conjunction with the accompanying drawing.

BRIEF DESCRIPTION OF THE DRAWINGS

FIG. 10 is a chart showing the effect on a shell egg of holding it at different temperatures for different lengths of time.

DETAILED DESCRIPTION OF THE INVENTION

Figure 1:
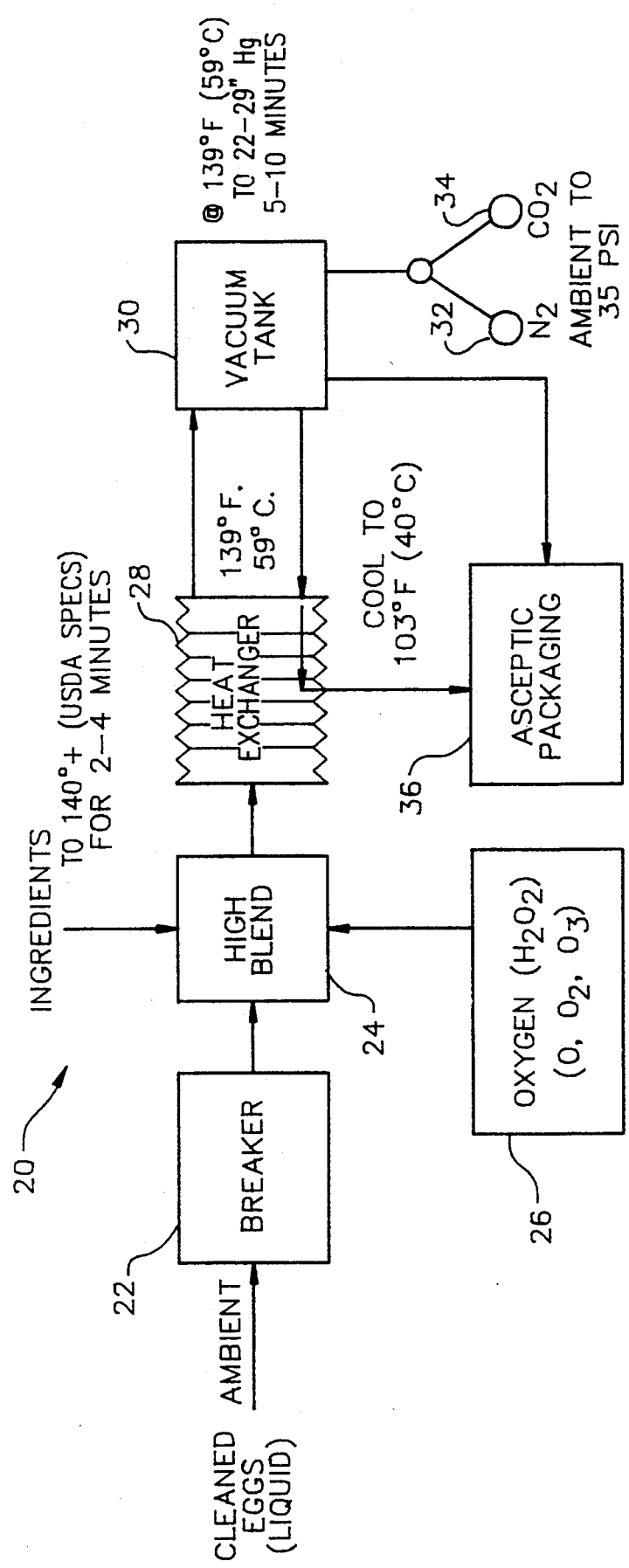
FIG. 1 is a schematic illustration of one system for treating liquid eggs and other products with comparable physical products in accord with the principles of the present invention; i.e., by hyperpasteurization.

The simplest form of HP processing is that used to treat shell eggs, liquid egg products including whole, yolk, whites and blends thereof, including egg substitutes, mayonnaise sauces, and other high moisture liquid or semi-liquid foods and food products.

In this application of hyperpasteurization, in the preferred form, shell or liquid egg is subjected to hypobaric pressure to substantially disinfuse indigenous dissolved gases. Preferred pressures are greater than 10" Hg. and preferably greater than about 22" Hg. for liquid egg and greater than 24" Hg. for shell egg. The liquid or shell egg may be heated to a temperature of from 129.9° F.

(54.4° C.) to no more than 150° F. (65.6° C.) for from 1 minute on the high temperature end to upwards of 3 hours on the low temperature end. A temperature of 139° F. (59.4° C.) for a period of time greater than 30 minutes and no more than 1.5 hours is preferred. The time and temperature selected depend primarily on the degree of microbial destruction desired and the degree of white thickening desired. Complete destruction of all Salmonella bacteria is a desirable objective with both liquid and shell eggs. To this end, a temperature of 139° F. for a period of 1 hour or more is preferred for both shell and whole liquid eggs.

Brief preliminary or even sporadic pasteurization above 139° F. (59.4° C.) can shorten the process time. When cold shell or liquid eggs are to be heated, they may first be exposed to common pasteurization times and temperatures to bring them up to temperature, where it is required by authorities, but the balance of the treatment should be at a temperature not to exceed 139° F.

For shell eggs, if thicker whites are desired, from about 0.5 to about 1.5 hours at between 130° to 139.9° F. (54.4° to 59.9° C.) will provide that end. Fifty minutes at 139° F. is preferred. The thickening of the writes, after about 75 minutes at 139° F., will be accompanied by some opacity in the whites due to commencement of cross-linking between the more heat labile portions of ovalbumins in the eggs. However, any total plate count at the end of the process can be expected to be Salmonella free while a longer duration will improve the egg product with respect to reducing any other types of microbial contamination present.

As a preferred final step, the shell egg or liquid egg product may be reinfused with ambient, purified ambient or inert gases which may be provided to the product in part or exclusively as it is repressurized from hypobaric to ambient or above. In some cases, it may be desirable to provide excess purified or inert gas(es) and continue to provide same to the hyperbaric side to insure maximum concentration in the interstices of the product.

While the foregoing approach will provide a reasonable degree of improved food safety, particularly with respect to destruction of Salmonella and to decreased oxygen tension if inert gases are used to replace indigenous ones, it cannot provide improved safety or keeping in the event of contamination by some other types of microbes or against very high initial concentrations of other microbes.

As discussed above, hyperpasteurization may often advantageously be carried out at an elevated temperature. The following example shows that one examplary food—fresh, raw, shell eggs—can be held at preferred temperatures for appropriate periods of time without significantly altering desirable characteristics of the eggs. This is apparent from FIG. 10 which also shows that unwanted changes occur if the time/temperature conditions heretofore proposed by others are employed.

Specific examples involving the treatment of raw, fresh, shell eggs follow.

EXAMPLE 1

Two dozen fresh shell eggs at 40° F. (4.4° C.) were placed in a 2-gallon controlled temperature water bath preset to 134.6° F. (57° C.).

Two dozen fresh shell eggs at 40° F. (4.4° C.) were placed in a 2-gallon controlled temperature bath which was filled with 2 gallons of peanut oil. The temperature of the bath was preset to 134.6° F. (57° C.).

At 5 minute intervals eggs were punctured with a stem thermometer while in place to determine the temperature at the center of the egg. At 5 minutes, eggs in both baths still averaged 40° F. (4.44° C.). At 10 minutes, eggs from both baths averaged 47° F. (8.33° C.). The 15 minute average for both was 67° F. (19.44° C.). At 20 minutes, the average temperature was 82° F. (27.78° C.). At 25 minutes, it was 98° F. (36.67° C.). At 30 minutes, the average was 113° F. (44.99° C.). At 35 minutes, the average temperature was 121° F. (49.44° C.). At 40 minutes, the average was 129° F. (53.89° C.) At 45 minutes, the average temperature was 134° F. (56.67° C.).

Target temperature at the center of the eggs of 129.9° F. (54.4° C.) was not achieved until some time between 40 and 45 minutes. The eggs held for this period of time showed no signs of occlusion of the white. Indeed, the white had thickened, making the egg appear fresher.

This phenomenon of white thickening without occlusion continued until about 1.5 hours had elapsed at which time a very slight but noticeable occlusion of white appeared. The appearance of the egg was very similar to that of a freshly laid egg which is somewhat lightly occluded after first being laid.

The white bunch-up around the yolk and the disappearance of thin running egg white continued up to 1.75 hours after which the egg became more noticeably occluded.

Eggs which had been held for 1.5 hours at 134.6° F. (57° C.) were equivalent to shell eggs held at 139° F. (59.4° C.) for 1.25 hours. The eggs were tested by a panel for raw appearance and were then prepared by frying, scrambling and poaching and tested for taste against controls. No significant differences were detected.

It was pointed out above that optimum results in hyperpasteurizing shell eggs maybe obtained by shaking or vibrating the eggs in the course of the hyperpasteurization process. The following example is directed to this aspect of the invention.

EXAMPLE 2

Three dozen shell eggs warmed to 139° F. (59.4° C.) were subjected to a vacuum of 28" Hg. for 10 minutes in a vacuum chamber.

After removal and while still very warm to the touch, the warmed eggs were taped in alignment longitudinally, and others were taped transversely, to the maximal arcual axis of an orbital shaker. The amplitude and frequency were varied over a range of 1/32" throw to ¼" throw at frequencies between 50 and 500 CPS for 5 minute intervals.

Upon opening, eggs which had been held for 7 to 10 minutes at between about ¼" and 7/16" throw were prescrambled in the shell, a significant and meritorious result.

The inside shell membrane was still intact. Heating seemed to facilitate even scrambling and, of course, facilitated contacting the shell with higher temperatures to effectuate speedier and more consistent contact with all portions of the inside of the gg. While cold eggs could also be scrambled, there was less uniformity of scrambling; and there appeared to be some internal shell membrane tearing. Warming to above 130° F. (54.44° C.) helped in this regard. Vacuum treatment of eggs weakened the internal membrane by stretching it and, at the same time, increased the volume of egg yolk by about 30%.

Several eggs were tested at much higher frequencies and shorter amplitudes, i.e., between about 1,000 and 1,200 CPS at 1/64" to 1/32" throw for about 15 minutes. A very unusual phenomenon occurred. Upon opening the shell, the egg had become almost entirely one large yolk, there being little or no distinct egg white inside the shell. After a few minutes on a flat surface, however, egg white began to slowly reappear from the yolk. Apparently, the white was worked through pores in the vitelline membrane by the vibrations. The membrane expanded without breaking to compensate for the much greater volume.

It goes, without saying, that identification of any bacteria present after processing is important in ascertaining the safety and keeping qualities of processed foods. The following example describes a microbial identification process which can be employed for that purpose with foods processed by hyperpasteurization.

EXAMPLE 3

Shell eggs for this test were selected for obvious surface filth, i.e., fecal matter, blood streaks, smudges, feather adherence and the like. Eighteen medium sized eggs selected from several thousand were rinsed in a 0.005% chlorine water solution. The eggs were immersed in a water bath preset to 139° F. (59.4° C.). Every 5 minutes, while in the water bath, the shell of an egg was punctured and a thermometer inserted into the center of the yolk. The egg was then removed, the shell was broken and the egg was dropped into a Petri dish for examination and preparation of culture samples.

The results are shown in Table 1.

TABLE I

| | Condition | Temperature | Millipore Culture Results |
|---|---|---|---|
| 5 mins. | White clear | Yolk/38° F. | <50/48 hrs. |
| 10 mins. | White clear | Yolk/39° F. | <100,000/48 hrs. |
| 15 mins. | White clear | Yolk/51° F. | 0/48 hrs. |
| 20 mins. | White clear | Yolk/74° F. | <9,000/48 hrs. |
| 25 mins. | White clear | Yolk/88° F. | <100/48 hrs. |
| 30 mins. | White clear | Yolk/101° F. | <50,000/48 hrs. |
| 35 mins. | White clear | Yolk/117° F. | <200,000/48 hrs. |
| 40 mins. | White clear | Yolk/129° F. | <50/48 hrs. |
| 45 mins. | Thicker | Yolk/135° F. | <10/48 hrs. |
| 50 mins. | Thicker | Yolk/139° F. | <20/48 hrs. |
| 55 mins. | Thicker | Yolk/139° F. | <40/48 hrs. |
| 60 mins. | Thicker | Yolk/139 F. | <10/48 hrs. |
| 65 mins. | Thicker | Yolk/139° F. | 0/48 hrs. |
| 70 mins. | Thicker | Yolk/139° F. | <10/48 hrs. |
| 75 mins. | Thicker, very slight occlusion | Yolk/139° F. | 0/48 hrs. |
| 80 mins. | Thicker, slight occlusion | Yolk/139° F. | 0/48 hrs. |
| 85 mins. | Thicker, slight occlusion | Yolk/139° F. | 0/48 hrs. |
| 90 mins. | Thicker, occlusion | Yolk/139° F. | 0/48 hrs. |

Additional tests have shown that, after 90 minutes in a 139° F. (59.4° C.) water bath, thickening and occlusion are pronounced and functionality of egg begins to fall off when tested against controls in meringues and sponge cakes.

Another useful category of information includes data on the presence of enzymes—especially catalase and peroxidase—and the enzyme activity level. Example 4 shows how processed eggs can be quickly tested for the presence of these enzymes and how the level of enzyme activity can be accurately estimated from the test.

EXAMPLE 4

Eighteen medium sized eggs were broke and emptied into 75 ml. test tubes which were then sealed with clear, sanitary, plastic wrap and rubber stoppers. The test tubes were placed in the water bath set at 139° F. (59.4° C.). Another 18 eggs were placed in a water bath set at 140° F. (60° C.). Every 5 minutes one tube was removed and set in a tube rack in ambient atmosphere.

The eggs were tested for the presence of catalase and peroxidase as follows: in a 25 ml. test tube, combine 12.5 mls. of egg white and 12.5 mls. of distilled water at 75° F. (23.9° C.). Using a standard 7 mm. paper punch, punch a disc from Whatman #1 filter paper. Using forceps, dip the disc into a 3% solution of hydrogen peroxide. Shake excess peroxide from disc, and insert the disc into the test tube beneath the surface of the diluted egg white. Release the disc, and time the disc as it falls in the tube. It should freely fall down the tube toward the bottom. As the absorbed peroxide reacts with the enzyme, free oxygen forms on the surface of the disc. The disc achieves neutral and positive buoyancy in a direct relationship to the amount of oxygen generated. Stop the watch when the disc has returned to the surface of the tube.

The time is directly proportional to the level of enzyme activity and is a quick test for enzyme presence and activity. Standard times range from 3 to 15 seconds. For every 10 second interval beyond 15 seconds, the peroxide treatment period is lengthened by about 5 seconds.

The results of the test for the presence of enzymes are summarized in Table 2.

TABLE II

| | Condition | Temperature at Egg Center | Peroxide/Float Catalase Activity Test Results |
|---|---|---|---|
| 5 mins. | White clear | 38° F. (3.3° C.) | High |
| 10 mins. | White clear | 45° F. (7.2° C.) | High |
| 15 mins. | White occluding against inside of tube | 51° F. (10.6° C.) | Medium |
| 20 mins. | White cooked inside 6–8 mm. | 60° F. (15.6° C.) | Medium |
| 25 mins. | White cooked inside 8–10 mm. | 80° F. (26.7° C.) | Medium |
| 30 mins. | White cooked inside 10–12 mm | 118° F. (47.8° C.) | Low |
| 35 mins. | White cooked inside 12–16 mm. | 135° F. (57.2° C.) | 0 |
| 40 mins. | White cooked inside 18–24 mm | 139° F. (59.4° C.) | 0 |
| 45 mins. | White cooked | 140° F. (60° C.) | 0 |

Following contact of the food being treated with an active specie of oxygen, it may be desirable to remove any oxygen remaining in the treated foodstuff to prevent oxidative degradation of the product. The following example shows how the evacuation of gases can be accomplished.

EXAMPLE 5

| Ingredient | Weight |
|---|---|
| Liquid whole egg or decholesterolized whole egg | 162.0 lbs. |
| Sodium carbonate | 0.07 lbs. |
| Carob gum | .05 lbs. |
| Xanthan | .05 lbs. |

-continued

| Ingredient | Weight |
| --- | --- |
| Citric acid | .07 lbs. |
| TOTAL | 162.24* lbs. |
| Optional: | |
| α-tocopherol* | 0.05 lbs. |
| Ascorbic acid* | 0.05 lbs. |

(*may be added for antioxidant protection during the oxygenation step if the food is sensitive to oxygen levels required during the process)
5 Cubic feet, 75%/25% nitrogen/carbon dioxide.

After leaving a plate pasteurizer, the eggs are pumped into a vacuum container where at least a portion of the gases entrained in the interstices of the liquid is removed by the vacuum exhaust. If the gases which have become trapped in the eggs are not removed, the egg products produced by this method are not natural, the principal problem being that the eggs are too soft and spongy when cooked. Disincorporating gases will restore natural cooked texture range to the egg products.

The temperature of the eggs during evacuation of the gases may be kept between 129° F. and 139.9° F. (53.9° C. to 59.9° C.) with 139.9° F. (59.9° C.) being preferred. However, temperature treatments adequate to meet USDA and other standards may be performed in the agitated vacuum pressure tank.

After sufficient gas has been removed by pumping down the vacuum chamber to from about 18" Hg. to 29.99" Hg. with 28.5" Hg. being preferred, the liquid eggs are pumped through the cold side of a heat exchanger and thereby cooled to between 33° F. to 54° F. (0.6° C. to 12.2° C. ), preferably to 40° F. (4.4° C.). Then, they are packaged, preferably aseptically.

The foregoing procedure is also good for egg substitutes and egg portions (yolks and whites). Egg whites tend to coagulate a little easier so it is preferred to drop the recommended high temperatures about 4 degrees, i.e., 139.9° to 135.9° F. (59.9° C. to 57.7° C.) when whites are processed.

The following examples deal with the hyperpasteurization of shell eggs and liquid whole eggs by a batch-type process and with the hyperpasteurization of liquid whole eggs by a continuous process.

The basic procedure is much the same for liquid and for shell eggs. The primary difference is that liquid products are circulated or agitated aggressively during the process. This is to ensure complete processing of all fluid, to prevent sticking to surfaces and to contact gases with all portion of the liquid.

Compared to controls, hyperpasteurized liquid whole eggs show some loss of thickness, probably due to substantial agitation. There is also a tendency for them to become off colored during baking when treated with phosphate or carbonate to compensate for processing functionality. The addition of citric acid protects against alterations in color as a result of the process.

Addition of, based on the weight of the product: (1) about 0.001% to 1.0% of a phosphate such as sodium phosphate monobasic, sodium phosphate dibasic, or sodium pyrophosphate or sodium carbonate, sodium bicarbonate or potassium analogs thereof; (2) potassium phosphates or carbonates (0.06% being preferred); (3) about 0.001% to 1.0% locust bean (carob) gum (0.03% being preferred); or (4) about 0.001% to 1.0% xanthan gum, 0.03% being preferred, all completely restore and, indeed, improve the functionality of hyperpasteurized liquid eggs. At this level, functionality is about 20% better than natural egg for making sponge cake. There is also greater volume and moisture in finished cakes prepared with hyperpasteurized eggs.

It typically requires 9 minutes to form a meringue from ordinary eggs. This is reduced to 5–6 minutes when hyperpasteurized eggs are used.

Locust bean gum is typically the principal ingredient employed for functionality restoration. Locust bean gum functions better when a synergistic hydrocolloid is used in conjunction with it. Any synergist such as xanthan gum, carrageenan, sodium alginate and the like can be used with minor adjustments in gum ratio and total concentration.

Treatment of the egg at the end of the cycle with 0.03% to 0.7% of citric acid restores color completely without interfering with taste or improved functionality. About an 0.07% concentration of teh citric acid is preferred.

Other acids, including lactic ($C_3H_6O_3$), can also be employed for color restoration and stability. Typically, from 0.001 to 1.00% of the acid will produce the desired results with 0.05% most often producing optimum results.

High speed agitation over short periods may be accomplished at the introduction point of the treating gases. This forces higher pressure gradients to develop between the liquid and gas, thereby providing more thorough contact and effectiveness of treatment.

A surface treatment prior to the initial hyperpasteurization step (vacuum treatment) consisting of 10 mgs. of cholesterol oxidase or cholesterol esterase in 100 mls. of water sprayed evenly over 12 dozen eggs resulted in totally different cholesterol contents of control egg serum and HP treated egg serum—900 mgs. per dl. vs. 700 mgs. per dl. as measured by enzymatic determination of cholesterol with a Hitachi 704. This is an approximately 27% reduction.

The reduction of cholesterol by the use of cholesterol oxidass and combinations of cholesterol esterase and cholesterol oxidass was even more significant when the enzymes were added to liquid whole eggs.

When 1 mg. of cholesterol oxidass was added to liquid eggs before HP processing in one test, the cholesterol content was lowered from 900 to 620 mgs. per dl., an approximately 31% reduction.

EXAMPLE 6

Selected crack-free, whole, fresh, raw, poultry shell eggs were washed in a mild chlorine solution, rinsed in sterile rinse water, surface dried, and then placed inside a vacuum/pressure vessel. These served as controls.

Shell eggs preheated to 139° F. (59.4° C.) in a hot water bath were placed in a vacuum/pressure container. The container was sealed and evacuated to 26" Hg. After holding it for 15 minutes at 139° F. (59.4° C.), the chamber was infused with sterile ambient air which had been preheated to 350°. (177° C.) for 1 hour, then cooled by way of a heat exchanger to 139° F. (59.4° C.).

After returning to ambient pressure, about 1 hour total elapsed time, the chamber was opened and eggs were removed and chill quenched in a bath at 32° F. (0° C.) for 15 minutes.

The total plate count of bacteria in the product samples averaged 50 per gm. All of the samples were Salmonella negative. When the controls were broken and tested, they averaged a bacterial count of 9,000 and were Salmonella positive.

The foregoing procedure was repeated using 8-oz. plastic juice containers filled with artificial liquid egg product containing 90% unpasteurized egg white. Microbiological culture results were as follows:

TABLE III

|  | Standard Plate | Count Per Gram |
|---|---|---|
| #1 Control, untreated | Untreated | +6,000,000 |
| #2 Control, untreated | Untreated | 31,000 |
| #3 Control, untreated | Untreated | +6,000,000 |
| #4 Control, untreated | Untreated | 340,000 |
| #1 HP, treated* | Treated | <10 |
| #2 HP, treated | Treated | <20 |
| #3 HP, treated | Treated | <30 |
| #4 HP, treated | Treated | <20 |
| #5 HP, treated | Treated | <10 |
| #6 HP, treated | Treated | <50 |
| #7 HP, treated | Treated | <10 |
| #8 HP, treated | Treated | <20 |
| #9 HP, treated | Treated | <10 |

*HP, treated — hyperpasteurized as described in this example.

EXAMPLE 7

A continuous system for minimal hyperpasteurization was set up for liquid whole eggs.

Three hundred lbs. of liquid whole eggs taken immediately after breaking were pumped into a sanitary holding tank or vat. A vertical tube mixer was affixed through the top lid of the sanitary tank. The tube was fitted with the oxygen infusion inlet of a tube through which a shaft turbine mixer was supported. The tube was connected to a compressed oxygen bottle. The compressed oxygen bottle was directed by a three-way valve so that all or a portion of the oxygen could be diverted through an ultraviolet chamber which exposed it to a 30 watt, 2,537 A ultraviolet bulb which was encased in a thin wall quartz sleeve. The oxygen was infused into the liquid whole eggs at a regulator setting of 12 psi through the ultraviolet chamber. Oxygen sampled from the head space in the vat showed an incoming ozone concentration in the oxygen of 0.0000025%.

The tubed turbine mixer was driven by a variable drive, high speed 3 h.p. air motor. The air motor was connected to a 5 h.p. air compressor and driven over a speed range of 1 to 3,600 RPM by adjusting an air inlet value.

A mix of oxygen ($O_2$) and ozone ($O_3$) was slowly admitted into the turbine as the eggs in the tank began to be mixed by the turbine action. The eggs entered the turbine at a port about six inches above the turbine and were impelled down the shaft and through the turbine blades. The rate of flow was adjusted by adjustment of the air motor speed. As the eggs began to mix, the mixing speed was adjusted by manipulating the valve until cavitation was encountered. At that point, the rpm was reduced to slightly below the cavitation point.

The incoming oxygen mixture was entrained by virtue of pressure into the recirculating liquid eggs and traversed in intimate contact with the oxygen across the turbine blades.

At that point, pressure at the blade surface would be expected to create high pressure and low pressure zones resulting in efficient contact between eggs and oxygen mixture. The contact was improved by recirculating the mixture across the turbine surface numerous times. The product was then degassed, filled with an inert gas, and aspectically packaged as described in detail below.

A useful alternative to the hyperpasteurization step just described is to introduce hydrogen peroxide ($H_2O_2$) into the eggs with agitation instead of the just-discussed mixture of air and oxygen. A 3% to 35% solution can be employed with a 20% solution being preferred. Between 0.005% and 2.00% $H_2O_2$ based on the volume of product can be used with 0.2% being preferred. The egg contains indigenous concentrations of peroxidases such as catalase which decomposes hydrogen peroxide. A foam or froth which is composed of nascent oxygen and oxygen will begin to form as the hydrogen peroxide is decomposed.

When this occurs and the product begins to turn pale yellow, mixing is reduced; and the product is transferred through a plate heat pasteurizer, raising the temperature to at least 140° F. for 3.5 minutes to meet USDA standards. The hydrogen peroxide is liberated by inherently present enzymes, eliminating the need to add enzymes as has been the case in prior art processes. This constitutes a major economy. In short, it has been found that sufficient concentrations of enzyme exist in natural egg to decompose any remaining hydrogen peroxide from that employed in hyperpasteurization of eggs and that these naturally present enzymes provide a cheaper, quicker, more efficient contact and destruction of microorganisms than those introduced into prior art process.

After the hyperpasteurization process step just described, the product is immediately conducted through aseptic piping into a vacuum chamber, and a vacuum is drawn to decrease the pressure in the chamber. At a pressure of about 20" to 22" Hg., the liquid egg begins to give up dissolved gases including free oxygen formed during the process. Disincorporation of the gases proceeds more rapidly as the vacuum is increased. A mechanical breaker is helpful in breaking the foam thus formed.

This process is carried out at about the temperature of the heat exchanger, 139° F. (59.4° C.) being the preferred temperature. A wide variety of temperatures can be employed, some being dependent upon regulatory requirements rather than practical limits. For example, in the previously outlined steps, actual working temperatures can range from a low of about 134° F. (56.7° C.) to a high of about 160° F. (71.1° C.) for short periods. However, in many instances, such as processes for treating pure egg whites, this temperature is not practical because it causes sticking and build-up of the product on the heat exchanger plates.

Immediately upon completion of disincorporation, fresh sterile air, nitrogen gas ($N_2$), carbon dioxide ($CO_2$), or a combination thereof may be introduced into the tank while the product is mixing. This produces, in the interstices of the liquid egg product, a non-contaminating, non-oxidizing atmosphere which inhibits unwanted oxidation-based spoilage. At this point, the product may be aseptically packaged.

When used to treat egg analogues which contain viable enzymes, the procedure is the same as just discussed. Of course, the liquid eggs and even analogue products can be pasteurized first before going through the foregoing procedures, and enzymes can be added as well as hydrogen peroxide.

Products processed with hydrogen peroxide must be free of the hydrogen peroxide at the completion of the process. The presence of hydrogen peroxide can be detected by testing for residual peroxidase activity in the product. The procedure is as follows: instill 25 mls. of 6% hydrogen peroxidase into a test tube. Dip a disc punched from Whatman #1 filter paper, using a standard 7 mm. paper punch, into the processed egg formulation, soaking the filter paper. Shake off the excess, and drop the disc into the test tube. The disc should descend to the bottom and should not rise back to the top for at least 3 minutes. If enzymes are present, the disc will rapidly rise to the surface.

A product hyperpasteurized as just described can also be improved in case there is undesirable color loss by the addition of acids including citric and ascorbic or carbon dioxide. A preferred acid is ascorbic acid. Ascorbic acid not only assists in color retention, but is also an antioxidant and can provide an extra measure of food component protection against oxygen. Functional restoration may also be required and can be obtained by the addition of selected gums, (hydrocolloids) and even distribution chemicals. Preferred gums are xanthan in combination with locust bean (carob) gum or any other synergist for locust bean or xanthan gum. Other gums can be used if they are not antagonistic in combination, such as is the case between acacia and sodium alginate, for example.

Preferred for the hydrocolloid gum(s) selected are amounts in the range of from 0.001% to 2.0%, based on the weight of the liquid product. 0.075% by weight is preferred when the xanthan and locust bean gum combination is selected.

Examples of suitable distribution chemicals are sodium carbonate ($NaCO_3$), monobasic sodium phosphate ($NaH_2PO_4$), sodium hexametaphosphate $[(NaPO_3)_x]$ and the like. Preferred is monobasic sodium phosphate in concentrations ranging from 0.001% to 1.0% based on the weight of the liquid product. A concentration of 0.03% is preferred.

Almost any liquid or semi-liquid food or feed product, including sauces, mayonnaises, and fruit and vegetable juices may be processed in this way to provide foods of improved safety. Alterations readily determinable by those skilled in the relevant arts to times, pressures and steps can be made depending on the specific characteristics of the product involved times, order of steps, advisability of additives and such. Feed products such as moist feed pellets can be stabilized and aseptically bagged.

EXAMPLE 8

Two groups of liquid eggs prepared as described above were infused with nitrogen gas by placing them at a pressure in the range of 26" Hg. to 20 psi. The pressure was held for 5 minutes and reduced to ambient by venting excess nitrogen gas, thus restoring the pressure on the eggs to ambient.

One group of eggs was treated in containers which were capped after treatment. The other group was treated in heat resistant plastic film which was sealed aseptically in the hyperpasteurization chamber.

When compared to controls prepared and filled in containers and then capped, the results were as follows:

TABLE IV

| Products Refrigerated at 45° F. | Immediate Colonies/ml. | 24 Hours Colonies/ml. | 48 Hours Colonies/ml. |
|---|---|---|---|
| Processed capped (12 8-oz containers averaged) | <50 | <100 | 500* |
| Processed aseptic bag (7 8-oz. containers averaged) | <10 | <10 | <10* |
| Unprocessed (control) | 2,000 | 5,000 | 7,000** |

TABLE IV-continued

| Products Refrigerated at 45° F. | Immediate Colonies/ml. | 24 Hours Colonies/ml. | 48 Hours Colonies/ml. |
|---|---|---|---|
| (11 8-oz containers averaged) | | | |

*Salmonella negative.
**Salmonella positive.

It was pointed out above that one advantage of hyperpasteurization, as used to treat shell eggs, is that oxygen species capable of reducing bacterial populations can be caused to migrate through the shell and other anatomical structures of the egg to its innermost parts, ensuring that even bacteria in those parts of the cell are killed. Examples 9 and 10 below deal with this aspect of the invention.

EXAMPLE 9

Four whole shell eggs were treated in a vacuum/pressure chamber at 139° F. (59.4° C.). A vacuum of 29.5" Hg. Was slowly drawn in the chamber over a period of 10 minutes. Then, bottled oxygen ($O_2$) was introduced to break the vacuum and pressurize the chamber to 45 psi over 5 minutes. After 10 minutes at 45 psi, pressure was released and the chamber returned to ambient atmospheric pressure. All eggs were intact.

The eggs were then cracked and examined. Oxygen had passed freely through the shell and membrane into internal yolk portions of the eggs.

EXAMPLE 10

Next, 4 dozen eggs were selected from the same lot as those employed in the Example 9 run. Two dozen were selected for treatment, and 2 dozen were kept for controls.

Selected eggs were placed in a sterile pressured vacuum chamber. The temperature inside the sterile chamber was 139° F. (59.4° C.). The chamber door was latched and made airtight.

The chamber was slowly evacuated from ambient pressure to a pressure of 29.5" Hg. over a period of several minutes with a two-stage rotary vacuum pump. Upon achieving the desired vacuum, the chamber was sealed by adjusting the vacuum exhaust valve.

Vacuum was held for about 5 minutes to permit interstitial gases entrapped n the egg to diffuse to the shell and through its pores into the chamber. Cracked shells are destroyed during this process.

The gas inlet valve was activated to break the vacuum and permit very slow entry of selected oxygen into the chamber. The treatment gas was bottled oxygen, 99.5% pure, channeled through a small, silent discharge arc where it was partially reacted to provide a small ozone concentration of 0.0001 to 0.10 volume percent. The gases traveled from the silent arc chamber through the gas inlet port into the treating chamber.

Eggs observed through a viewing port and removed at different stages of the operation show that the following occurs. Air in the space between the egg membrane and shell is evacuated. The membrane moves into complete contact with the interior of the shell as the air is drawn through the pores.

The thicker portion of the whites is drawn away from the yolk into closer proximity to the shell membrane. The yolk sac membrane expands to follow the white into closer proximity to the shell. The expansion of the yolk membrane and yolk sac material is on the order of 25% to 30%, depending on the degree of vacuum achieved. Free gases begin to expand as the liquids are pulled outward, forming free gas bubbles. These gravitate toward the inside membrane surface and slowly diffuse through the membrane and then the shell pores.

Infrared gas analyses of these gas indicate that they contain oxygen ($O_2$), nitrogen ($N_2$), and carbon dioxide ($CO_2$) with sometimes minute amounts of sulfur-bearing gases.

At this point, the maximum temperature of the egg, about 139° F. (59.4° C.), permits more rapid disinfusion. Vibrations in the chamber or chamber plate also facilitate and speed up this removal of gases from the egg.

As the nascent oxygen (O), oxygen ($O_2$), and ozone ($O_3$) enter the chamber, the disinfusion of the egg liquid slows; and the relative vacuum begins to drop. The process proceeds very slowly until the chamber has been restored to ambient pressure with gases containing a high concentration of oxygen and small concentrations of ozone ($O_3$). If hydrogen peroxide is used on the outside of shell eggs or in a bath in which the shell eggs are placed before evacuation, it can also be forced through the pores at very low hypobaric pressure.

The gas entry valve is left open, and the silent arc generator is bypassed by adjusting oxygen inlet Valves. The oxygen continues to fill the chamber, and the internal chamber pressure builds. Chamber oxygen transits the shell through its pores as the pressure builds. Under maximum hypobaric vacuum, the egg has given up most free interstitial gas. As hypobaric vacuum is released, the egg stabilizes by taking up excess oxygen in the chamber.

As pressure builds, hyperbaric pressure infuses chamber gases through shell and membrane pores into the egg liquid until equilibrium is achieved between the egg and chamber pressure. Very high concentrations (saturation levels) of oxygen ($O_5$) and ozone ($O_3$) are now present, these species being diffused throughout and in the interstices of the egg. The introduction of pressurized oxygen is continued at a pressure of from about 5 to 65 psi, 40 psi being preferred.

Treated eggs hyperoxygenated with more or less pure oxygen levels at 45 psi and above develop a noticeable taste sensation best described as somewhat acidic and somewhat effervescent.

At this stage, the egg is equilibrated by holding it at maximum oxygen pressure for at least several minutes. The chamber is sealed during this stage by adjusting the gas inlet valve to the "off" position.

The vacuum pump is activated, and the vacuum exhaust valve is opened to permit the vacuum to withdraw all chamber oxygen. This is accomplished slowly to allow the egg sufficient time to equilibrate by the escape of gases through its membrane and shell.

The vacuum is drawn over the range of 15" Hg. to 29.9" Hg. About 28" Hg. is preferred. Any remaining nascent oxygen (O), oxygen ($O_2$) and ozone ($O_3$) which has not been taken up is disinfused from the egg and evacuated through the vacuum pump.

Scanning infrared samples of these gases show little or no nascent oxygen (O) or ozone remaining.

Again, hypobaric vacuum is employed for several minutes to provide time to equilibrate the egg.

Purified bottled nitrogen gas ($N_2$) may then be bled into the chamber. The gas inlet valve is opened slightly, breaking the vacuum and permitting the slow inlet of nitrogen.

Nitrogen is fed into the chamber until at least ambient pressure is reached. Pressurization may be continued, preferably to a pressure of about 20 psi. The presence of a high concentration of nitrogen from the hypobaric through the hyperbaric cycle results in the replacement of a majority of depleted gas and oxygen in the egg with nitrogen.

The egg is removed from the chamber, cooled to 104° F. (40° C.) in ice water, optionally marked by rubber stamp with an indicator dye to show if conditions that might make the egg unsafe to eat or that would otherwise effect its usability have developed, and preferably then treated with a pore sealant.

One suitable indicator dye is resazurin, which is normally green. However, upon exposure to reducing agents, it becomes red. If applied to its surface before coating the shell, resazurin dye can indicate that conditions inside the yolk have changed. If nitrogen gas ($N_2$) or carbon dioxide ($CO_2$), for example, is released as would happen if the shell cracked, the effects of gas transfer and the presence of reducing bacteria change the color of the dye. Other indicators, including dyes, can be used depending upon the degree of sensitivity and colors required and such. Resazurin is preferred.

Cooling may be accomplished directly in a stream of cool air or by immersion in chilled water. It is preferable to cool the egg only after adding the pore sealant so that the vacuum created as the egg cools does not serve to draw in any surface contamination which may have been caused by handling after the preceding hyperpasteurization steps but will instead draw the pore sealant against the surface of the shell, helping to lodge it in the shell pores.

While not required, the use of a pore sealant is preferred to prevent recontamination of the egg through the pores by microbes and to prevent inert gas escapement during storage. Edible oils, waxes, paraffins, silicates, silicones, film forming polymers and even solid alcohols and such may be used. The preferred material is a combination of palm stearins and vitamin E ($\alpha$-tocopherol) mixed 5 parts palm stearins to 1 part vitamin E oil. Palm stearins is preferred due to its high saturation, high melting point, overall durability and favorable cost. Vitamin E is preferred due to its natural antioxidant properties. Either palm stearins or vitamin E may also be used alone.

Throughout the process, the temperature is maintained as closely as possible to 139° F. (59.4° C.). As in traditional pasteurization techniques, this temperature can be varied upward or downward provided that critical time-temperature relationships which are know to cook or coagulate egg albumen are not exceeded. Other aspects of the process can be performed with a shortened or lengthened overall process framework which willshould be obvious to one skilled in the art.

Other inert gases may be used either alone or in combination for shell eggs. They are typically employed only under particular circumstances, however. Such a circumstance is where it is desirable to influence Haugh unit values favorably. Carbon dioxide ($CO_2$) may be used alone or with nitrogen ($N_2$) for stability. Carbon dioxide is acidic and influences the character of the albumen of the egg white, which undergoes changes at a pH ranging from about 8 up to as high as 11, depending on the age and condition of the shell egg. The preferred range of additive when its use is desirable is 9 parts nitrogen gas to 1 part carbon dioxide.

The shell eggs produced by the foregoing process exhibit some differences from controls. Bacteriological tests show the hyperpasteurized shell eggs to have a much reduced count, or even be free, of microbes present in controls.

MRI (Magnetic Resonance Imagine) tests conducted on hyperpasteurized shell eggs and controls reveal no differences between processed and control samples. MRI was employed to study possible differences in free radicals, sulfhydryls, amino acids, proteins, and fatty acids.

Physical differences between treated and untreated control shell eggs are:

The treated shell is "off" white;
The pores of the treated shells are visible to the naked eye;
The treated shell inside has a milder odor;
The treated egg has an improved Haugh unit value;
The treated egg appears to have a larger yolk;
The treated egg has a yolk which appears more transparent;
The treated egg has a milder taste;
The treated egg has a vastly improved shelf life;
The treated egg white may be somewhat firmer;
The treated egg is a safer food.

Haugh unit reflects the degree of egg white thickness and bunch-up around the yolk. It relates egg weight and height of thick albumen, is the most widely used measurement of albumen quality, and was proposed by Raymond Haugh in 1937. This method involves measuring the height of the thick albumen. Care must be taken to get a reading with the contact arm not touching the chalaza; otherwise the reading will be too high. "The higher the Haugh value, the better the albumen quality of the egg," is a generally accepted statement. Originally, the determination of Haugh units (H.U.) was a time-consuming operation involving collecting measurement data and application of the formula:

$$\text{Haugh units} = 100 \log \left[ H - \frac{\sqrt{G}\, 30W^{0.37} - 100}{100} + 1.9 \right]$$

where:
H is the albumen height (millimeters),
G is 32.2, and
W is the weight of egg (grams).
The expression:

$$((\sqrt{G}30W^{0.37}-100)/100)+1.9)$$

equals zero when the egg weight is 56.7 g. (2 oz.).

The calculation of Haugh units was speeded up by the development by Brant et al. (1951) of an interior egg-quality calculator for the rapid conversion of egg weight and albumen height data to Haugh units.

The following tables compare the bacterial populations of liquid whole eggs and shell eggs, both hyperpasteurized as discussed in this example, with the bacterial populations of controls. The test were made by independent laboratories.

TABLE V

| | Control | Hyperpasteurized |
|---|---|---|
| Liquid Whole Eggs expressed in colonies per ml.; 3-cc sample | +250,000 | 50 |
| Liquid Whole Eggs expressed in colonies per ml.; 3-cc sample | +250,000 | 100 |
| Liquid Whole Eggs expressed in colonies per ml.; 3-cc sample | 7,000 | 0 |
| Liquid Whole Eggs expressed in colonies per ml.; 3-cc sample | 50,000 | <10 |
| Liquid Whole Eggs expressed in colonies per ml.; 3-cc sample | 2,000 | 0 |
| Liquid Whole Eggs express in colonies per ml.; 3-cc sample | +100,000 | 0 |
| Shell Eggs expressed in colonies per ml.; 3-cc sample | 100 | 0 |
| Shell Eggs expressed in colonies per ml.; 3-cc sample | 100 | 0 |
| Shell Eggs expressed in colonies per ml.; 3-cc sample | 5,000 | 0 |
| Shell Eggs expressed in colonies per ml.; 3-cc sample | 100 | 0 |
| Shell Eggs expressed in colonies per ml.; 3-cc sample | 50,000 | 50 |
| Shell Eggs expressed in colonies per ml.; 3-cc sample | 7,000 | 0 |

TABLE VI

RAM ™ TESTS

| | 24 HOURS | 48 HOURS |
|---|---|---|
| #230: Syringe C1, tested for salmonella and standard plate count | 0 | 0 |
| #231: Syringe C2, tested for salmonella and standard plate count | 0 | 1,000 no. S. |
| #232: Syringe C3, tested for salmonella and standard plate count | 0 | 1,000 no. S. |
| #233: Bag sample #3, whole egg, raw | some growth | +100,000 E. coli; no. S. |
| #234: Bag sample #3, whole egg, salmonella positive | some growth | +100,000 no. S. |

| | Cholesterol Content |
|---|---|
| #235: Whole egg in shell, #H2T | 620 mgs. |
| #235: Whole egg in shell, #H1T | 900 mgs. |
| #237: Bottled sample, whole egg | 722 mgs. |

The previous examples deal with the hyperpasteurization of liquid eggs and raw shell eggs. The following examples demonstrate that hyperpasteurization is equally applicable to other liquid and solid products including such large solids objects as whole chicken carcasses. These tests also illustrate representative process modifications—for example, the use of carbon dioxide instead of nitrogen to prevent oxidative degradation of the product.

EXAMPLE 11

Chopped raw poultry pieces such as legs, thighs, breasts, backs and wings may be treated by essentially the same hyperpasteurization procedure as shell eggs. The pieces are somewhat defatted during the process if held at 139° F. (59.4° C.).

Whole fresh raw poultry carcasses are hung inside the chamber rather than laid on surfaces. This is to ensure equal gas infusion at all points of the carcass. The temperatures can be reduced to eliminate defatting. The preferred low temperature is 100° F. (37.8° C.). A preferred moderate heat temperature, particularly for fat-reduced poultry, is 139° F. (59.4° C.). Smoked and baked poultry have also been processed.

Surface, cavity and bone swab cultures show a reduction in bacterial count of whole carcasses ranging from 95% to 100%. TABLE VII shows typical swab test results after 24 hours growth of the bacteria removed by the swabs in a commercial peptone broth culture medium.

TABLE VII

| Petri dish cultures | Before HP | After HP |
| --- | --- | --- |
| Surface swab | heavy growth | no growth |
| Cavity swab | very heavy growth | no growth |
| Flesh to bone, leg | heavy growth | no growth |
| Flesh to bone, back | medium growth | scant growth |
| Control Petri dishes: | No HP | |
| Surface swab | heavy growth | |
| Cavity swab | heavy growth | |
| Flesh to bone, leg | medium growth | |
| Flesh to bone, back | medium growth | |

Processed whole carcass poultry, freshly hyperpasteurized per the foregoing procedure, has an off color compared to the controls. The breast seems to be flatter. The obvious pores on the skin, particularly noticeable around the vent and upper thighs, are considerably reduced or absent. When weighed before and after HP, there is no difference. The hyperpasteurized poultry is considerably less attractive than the control before cooking. As discussed above, the fat content of the hyperpasteurized product may be lower. This is shown by the data obtained from a representative run and presented in TABLE VIII.

TABLE VIII
DECANTED FAT FROM COOKED CARCASSES

| Carcass | Before Cooking | After Cooking | Total Fat | Total Water |
| --- | --- | --- | --- | --- |
| Before HP | 62.3 ozs. | — | — | — |
| After HP | 62.3 ozs. | 49.3 ozs. | 51 mls. | 65 mls. |
| Control | 60.5 ozs. | 47.0 ozs. | 24 mls. | 85 mls. |

A hyperpasteurized roasting chicken processed as described in this example and a control roasting chicken, each weighing 66 ozs. (4 lbs. 2 ozs.), were cooked side-by-side in a convection oven at 375° F. (190° C.) for 50 minutes. The appearances of the cooked chickens are radically different. The HP carcass stands up more firmly. The skin is more evenly browned. The skin on the legs and breast of the control is wrinkled, while the skin of the HP bird is taut and smooth.

Upon removing the skin, the breast of the HP birth is found to be very white with an attractive pinkish overtone. That of the control is slightly "off" white to brownish. The breast meat from the HP bird is more tender than that of the control, but the control bird breast is judged slightly juicier than the HP breast. The taste and aroma of the HP bird is somewhat milder than the control.

After being kept in sealed polyethylene bags in a refrigerator over night, the odor difference is considerably more pronounced. The HP bird is preferred by testers.

When all free fat from each bird is decanted into separate beakers, the juices from the hyperpasteurized bird contain approximately twice the quantity of fat that the control bird juices contain; i.e., control bird, 25 mls. and HP treated bird, 54 mls.

There were no other noticeable differences between the treated and untreated poultry except slightly greater tenderness and some greater defatting when hyperpasteurization was conducted at higher temperatures.

EXAMPLE 12

Two whole poultry carcasses were hyperpasteurized, substituting carbon dioxide ($CO_2$) for nitrogen gas ($N_2$). Before processing, carcass no. 1 weighed 1,253 gms., and carcass no. 2 weighed 1,144 gms. Two controls, carcasses no. 3 and no. 4, weighed 1,203 gms. and 1,028 gms. respectively.

After processing, carcass no. 1 was considerably more similar in appearance to the control carcasses than carcasses processed using infused nitrogen gas. Carcass no. 1 had a natural color and was similar in overall appearance to the control. Differences in the processed carcasses were noticeable but not marked.

Carcass no 1 and control no. 2 were convection oven cooked for 60 minutes at 375° F. (190° C.) in glass baking containers. Overall container dimensions were $12'' \times 4'' \times 6''$. Upon removal from the oven, the free juices were poured from each container into a measuring graduate.

The volume of fat and juices was nearly the same for both processed and unprocessed carcasses; i.e., 40 mls. of juice and 25 mls. of free fat for the hyperpasteurized chicken and 38.5 mls of juice and 23 mls. of free fat respectively for the control.

Visual and organoleptic qualities of the HP processed chickens were evaluated under controlled conditions by a panel of testers. The results appear in TABLE IX.

TABLE IX

| | Visual | Taste | Juiciness | Tenderness |
| --- | --- | --- | --- | --- |
| HP processed carcass | 8 | 8 | 9 | 9 |
| Control | 8 | 8 | 8 | 8 |
| Score (composite of testers) | 1-4 (poor) | 5-6 (fair) | 7-8 (good) | 9-10 (excellent) |

The breast meat was not white with a pinkish hue, as other hyperpasteurized chicken had been, but was exactly the same in appearance as the control.

The use of carbon dioxide ($CO_2$) to replace nitrogen gas ($N_2$) resulted in marked changes, restoring almost complete equivalence between control and HP processed birds, both before and after processing and cooking. While the HP processed bird showed some visual signs of processing after preparation, it outscored the control in both tenderness and juiciness of meat.

Surface swabs of the carcasses before processing no. 1 showed an average microbial count of 12,000 colonies per 3-M Petrifilm Aerobic Count Plate Test for birds nos. 1 and 2, respectively.

Swab values of carcass no. 1 after processing was —0— plate count versus a 280,000 plate count for the control after culturing for 48 hours at 95° F. (35° C.).

Addition of carbon dioxide ($CO_2$) instead of nitrogen gas ($N_2$) improves the appearance considerably. A combination of approximately equal parts of nitrogen gas and carbon dioxide, however, is preferred.

EXAMPLE 13

Two thousand (2,000) mls. of 3% homogenized milk taken from a 1-gallon grocery carton container was divided and poured into two 1,000-ml. beakers.

One beaker was refrigerated as a control. The other beaker was placed in a vacuum/pressure chamber. The temperature was set at 100° F. (37.8° C.), and the chamber was evacuated to 29.1" Hg. After a period of 5 minutes, oxygen ($O_2$) containing 15 ppm ozone ($O_3$) at a regulator setting of 40 psi was infused through the vacuum breaker valve into the chamber. At 45 psi on the vacuum/pressure chamber gauge, oxygen ($O_2$) and ozone ($O_3$) were valved off.

The product was held for ten minutes at 40 psi and 100° F. (37.8° C.) to provide equilibration of gas throughout sample. Upon completion of the 10 minute cycle, the chamber was evacuated to 29.1" Hg. to disinfuse oxygens. The vacuum was held for 5 minutes to allow for complete disinfusion of all possible nascent oxygen (O), oxygen ($O_2$), and ozone ($O_3$).

After the 5 minute disinfusion step was completed, nitrogen gas ($N_2$) at 33 psi was infused through the vacuum breaking valve until the pressure gauge on the vacuum/pressure chamber showed 33 psi. The 33 psi pressure was maintained for 5 minutes to provide for complete absorption of the nitrogen gas by the sample.

A vacuum release valve was then opened, and excess nitrogen gas ($N_2$) was vented to ambient pressure. The processed sample was removed and refrigerated.

Twenty-five ml. samples of the control and hyperpasteurized milk were taken. To these was added a stock solution of 2% methylene blue (a bacteriological stain)/98% distilled water. The samples were placed in a water bath at 98.6° F. (37° C.) and examined every 15 minutes. The control sample returned to its original color in 45 minutes. The hyperpasteurized sample did not change color in 3 days. This shows that the bacterial population of the processed milk had been drastically reduced, if not substantially eliminated.

Sensory tests of the milk yielded the following results:

TABLE X

| Control: | Preferred over the HP milk by 8 testers |
|---|---|
| HP Processed: | Preferred over the control by 8 testers; 6 testers detected an abnormal taste in the HP processed sample; 10 thought both samples tasted normal but that hyperpasteurized had a stronger milk flavor than did the control |

The test was repeated with the ozone ($O_3$) concentration reduced to 1.25 ppm and nitrogen gas ($N_2$) diluted 50% with carbon dioxide ($CO_2$) substituted for the straight nitrogen used in the preceding run. The testers had the same preferences, but no testers could detect any abnormal flavor in the HP processed milk.

Various ones of the process steps employed in hyperpasteurization and described above can be employed on their own to accomplish objectives of significant value. For example: (1) infusion of a shell egg with an inert gas followed by sealing of the shell pores can be employed to improve the keeping quality of the egg; (2) holding a shell egg under the time and temperature conditions identified above can often, and without more, significantly reduce the bacterial population inside the egg shell without causing undesirable coagulation of the egg white; and (3) holding shell eggs, liquid eggs, and liquid egg products under the specified time and temperature conditions can result in the egg or egg product appearing fresher by causing the egg white to thicken without coagulating the white to any substantial extent. These representative, and other process steps and combinations of process steps that may be employed in hyperpasteurization are therefore considered inventive in their own right and are fully intended to be covered in the patent coverage sought in the appended claims.

Of particular importance, in this respect, is the application of hyperpasteurization to shell egg, or liquid egg products and blends. There are circumstances in which hyperpasteurization of these and comparable products can be effected simply by holding them for longer times at lower temperatures than heretofore employed for conventional pasteurization by increasing the time at the low temperature. This accomplishes important and unique objectives—typically an egg product with improved keeping qualities and fresh appearance.

Thus, in the foregoing and other applications of the invention, by processing the product being treated at temperatures and times taught to be unimportant or ineffective by Swartzel et al. and others, the objectives sought by earlier workers can be realized, typically with improved results, at lower cost, or with these and other important advantages. Thus, not only is hyperpasteurization not unanticipated by what has gone before but actually operates counter to what is taught by the prior art.

Referring now to the drawings, FIGS. 1–8 depict systems in which the several processes discussed above in varying levels of detail and exemplified in the working examples may be carried out. The system 20 illustrated in FIG. 1 is particularly designed for the hyperpasteurization of liquid eggs. It can be employed for the hyperpasteurization of other liquid products as well. In that case, the unit 22 employed to break the eggs is omitted or simply not employed.

In addition to the conventional egg breaker unit 22 just described, hyperpasteurization system 20 includes a pressure/vacuum type reactor 24 with a source 26 for an active form of oxygen, a heat exchanger 28, a vacuum vessel 30, sources 32 and 34 for respectively supplying nitrogen and carbon dioxide to the vacuum vessel, and an aseptic packaging unit 36.

Liquid eggs are transferred from breaker unit 22 to vacuum/pressure unit 24. An active form of oxygen (atomic, molecular, peroxide, or ozone) is introduced into unit 24 and incorporated in the liquid eggs with agitation to reduce the microbial population of the product.

From this unit, the eggs are transferred to heat exchanger 28. Here they are held, typically for 2–4 minutes at a temperature of 140° F. Generally, this step need be employed only to meet USDA and other standards because the preceding step will have destroyed substantially all Salmonella and other harmful microbes in the product.

The heat exchanger can also be employed to subsequently cool the eggs to a temperature appropriate for packaging and other steps.

From the heat exchanger, the treated product can be transferred directly to packaging unit 36. This unit is preferably operated under aseptic conditions so that harmful microbes will not be reintroduced into the product.

Alternatively, the product may be transferred from heat exchanger 28 to vacuum tank or vessel 30. In this unit, oxygen-containing gases and the product are removed and replaced with nitrogen, carbon dioxide, or a mixture of those gases. As discussed above, this significantly improves the keeping quality of the product by materially reducing its susceptibility to oxidative degradation.

From vacuum vessel 30, the product is transferred to packaging unit 36. Again, this unit is preferably operated under aseptic conditions to avoid the reintroduction of harmful microbes.

Figure 6:
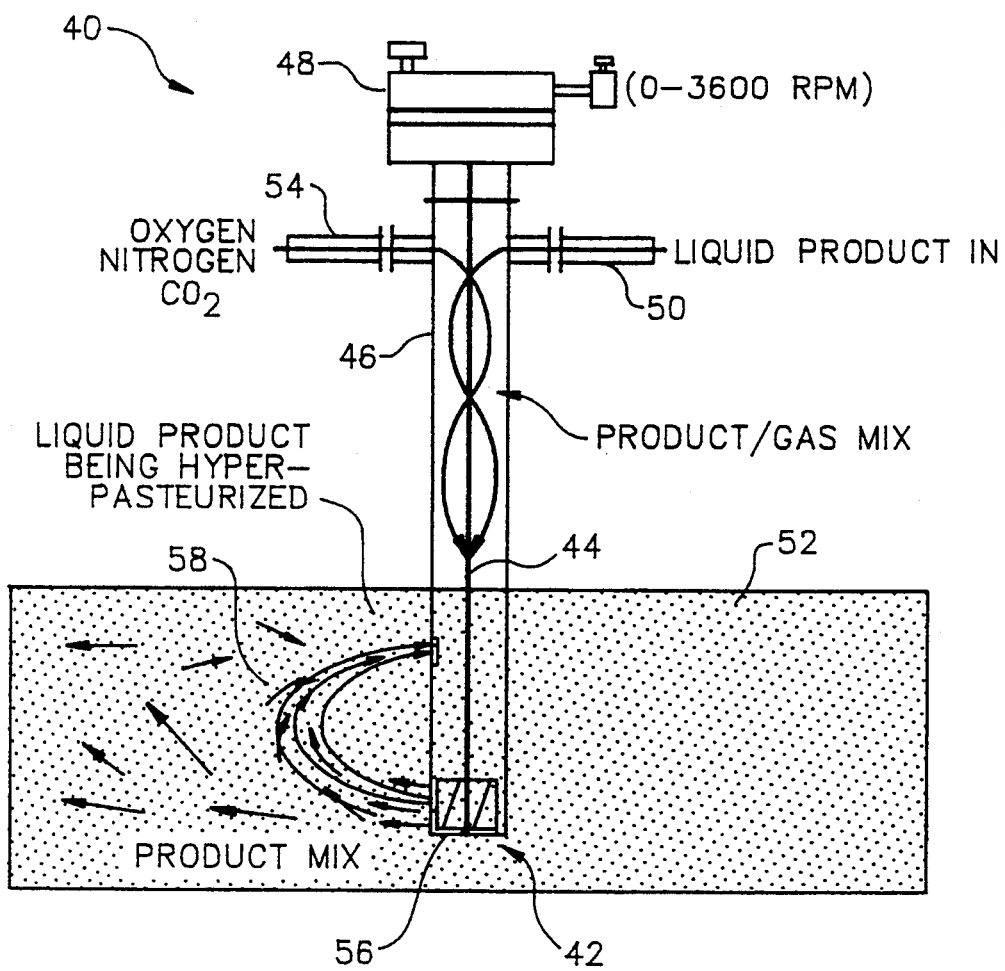
FIG. 6 is a partially pictorial view of one reactor which can be employed, in accord with the principles of the present invention, to contact a liquid food with one or more species of oxygen in a manner which will result in efficient destruction of harmful bacteria present in the food; inert gas may subsequently introduced into the reactor and into the interstices of the treated product to protect it from oxidative degradation.

One vacuum/pressure unit which can be employed to advantage in system 20 and other systems for hyperpasteurizing liquid products is shown in more detail in FIG. 6 and identified by reference character 40. In addition to a tank or shell (not shown), this unit includes a turbine type agitator or impeller 42 driven through a shaft 44 housed in a hollow conduit or pipe 46, typically by the illustrated adjustable speed air motor 48. An inlet line 50, tapped into conduit 46, is employed to fill the reactor with the liquid product 52. The selected, active form or forms of oxygen are introduced under pressure through a second inlet line, also tapped into conduit 46. The oxygen is discharged through the lower, open end 56 of pipe 46 and is intimately mixed with the liquid product 52 as indicated by arrows 58.

Figure 2:
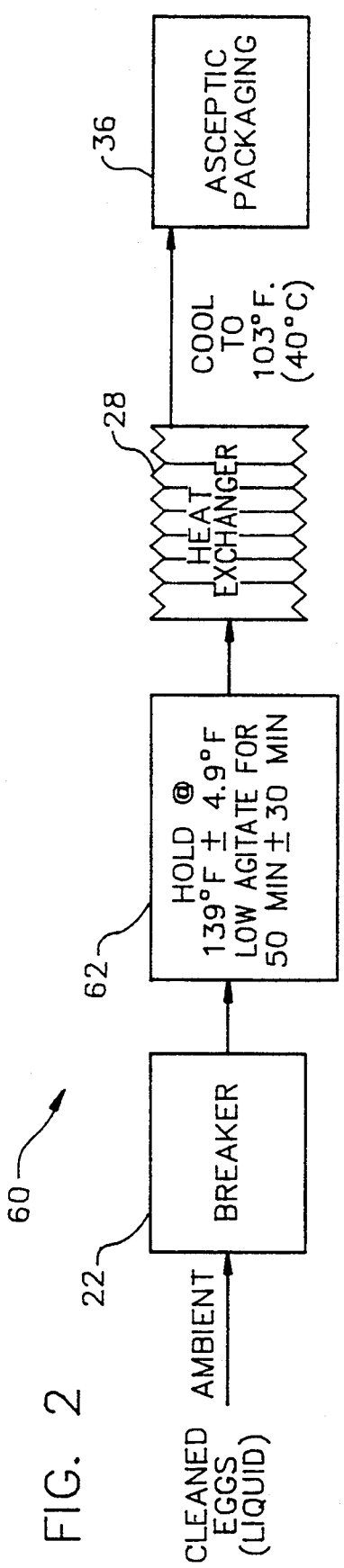
FIG. 2 is a view, similar to FIG. 1, of a second system for hyperpasteurizing liquid eggs and other products with comparable physical characteristics.

As pointed out above, it has unexpectedly been found that, in many cases, the microbial content of liquid products such as eggs can be reduced to more than acceptable levels by holding them under time/temperature conditions which do not adversely affect the functionality of the egg—by coagulating the egg whites, for example. A simplified process which can be employed for this purposes is illustrated in FIG. 2 and identified by reference character 60. This system includes the above-discussed egg breaker 22, a holding tank or vessel 62, heat exchanger 28, and aseptic packaging unit 36.

Eggs broken in breaker 22 are transferred to tank 24 where they are held at a temperature lower than that heretofore thought acceptable for times longer than those taught by the prior art to eliminate harmful bacteria from the product without impairing its functionality. Mild agitation may improve the effectiveness of this process step. If so, a reactor with a variable speed agitator—for example, the reactor 40 illustrated in FIG. 6—may be employed.

From the holding vessel, the treated product is transferred to heat exchanger 28 where it is cooled to a temperature suitable for packaging. Thereafter, the cooled product is typically, although not necessarily, transferred to packaging unit 36. If the product is to be packaged, this will preferably be done under aseptic conditions for the reasons discussed above.

Figure 3:
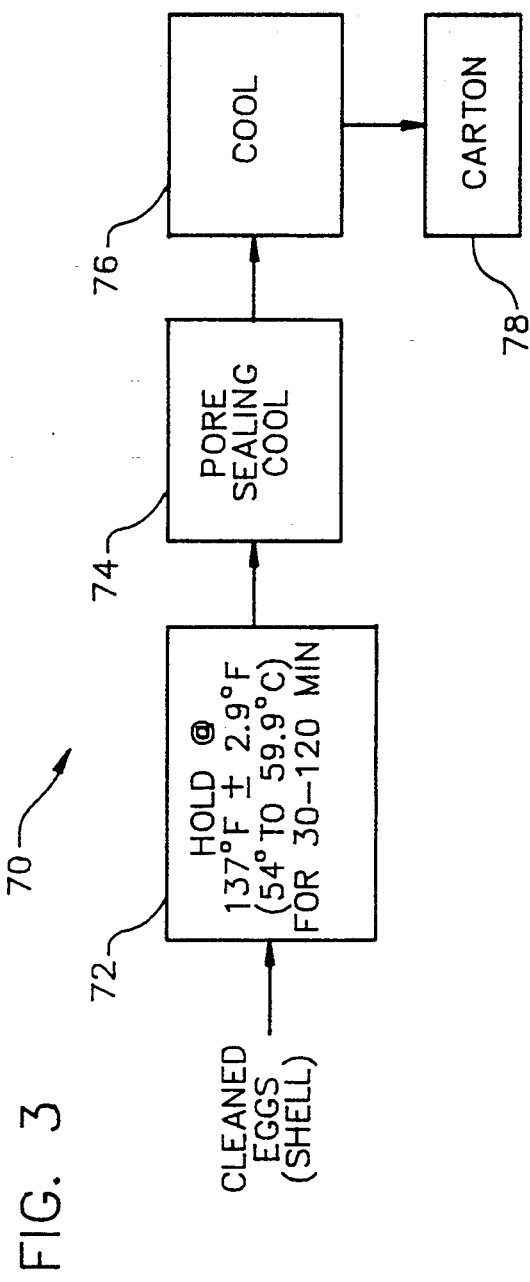
FIGS. 3–5 are views, similar to FIG. 1 of systems for hyperpasteurizing solid foods such as shell eggs, poultry, to-be-frozen entrees, hamburgers, etc.

Another process employing the principles of the present invention and disclosed in the working examples and elsewhere above is designed to make poultry eggs safer to eat without impairing the functionality of the eggs by holding the shell eggs under time/temperature conditions which will destroy harmful bacteria inside the egg shells. One system in which a process of this character can be carried out is illustrated in FIG. 3 and identified by reference character 70. That system includes a holding vessel or tank 72, an optionally employed pore sealing unit 74, a heat exchanger 76, and a packaging unit 78.

As is discussed elsewhere in this specification, the initial step in treating whole eggs in a system like that identified by reference character 70 is to clean, and typically disinfect, the outer surfaces of the egg shells.

The cleaned eggs are transferred to tank 72 where they are held at the temperature and for the time selected to reduce the microbial population of the eggs.

Thereafter, the treated shell eggs can be transferred to heat exchanger 76 to reduce their temperature to a level appropriate for packaging. Then, the now cooler eggs are transferred to packaging unit 28 where they are placed in cartons or other containers.

Optionally, the pores and the Shells of the treated eggs can be treated with palm stearine or another of the sealing agents identified above before they are packaged in unit 74. This keeps oxygen-containing and other unwanted gases from penetrating through the pores in the egg shells to the interior of the egg, thereby reducing degradation and improving the keeping quality of the treated egg.

Figure 4:
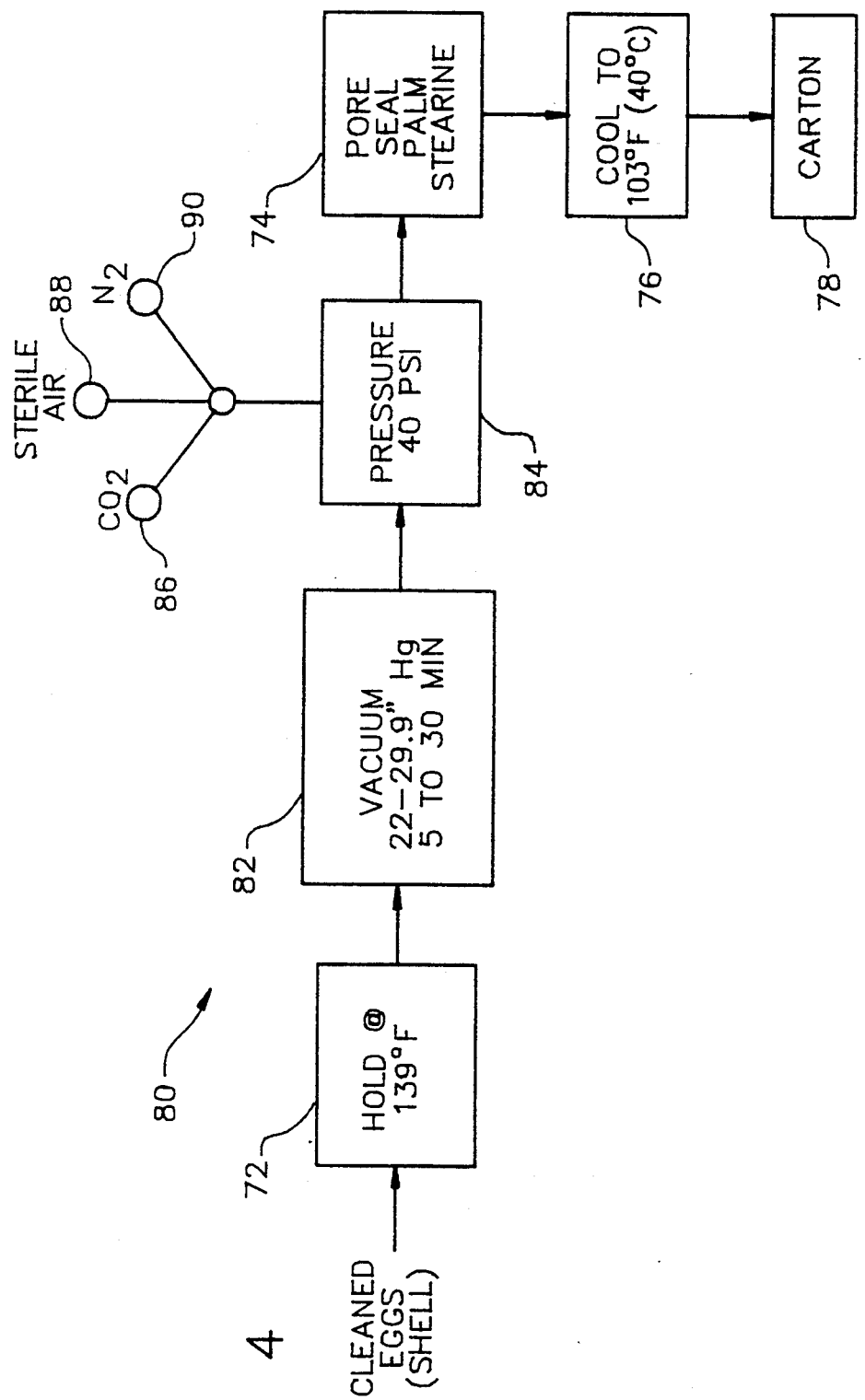

It was also pointed out above that the keeping quality of eggs treated in the manner just described can often be even further improved by evacuating existent or indigenous, degradation promoting gases from the interior of the egg shell, and replacing the evacuated gases with inert gases before the pores of the egg shell are sealed. A system for carrying out this process is illustrated in FIG. 4 and identified by reference character 80.

That system includes holding tank 72, vacuum vessel 82, pressure vessel 84, sources 86, 88, and 90 of carbon dioxide, sterile air, and nitrogen, pore sealing unit 74, heat exchanger 76, and packaging unit 78.

Cleaned and treated eggs are transferred from holding tank 72 to vacuum tank 82. Here, they are held under negative pressure for a period long enough to draw the unwanted, indigenous gases from the interior of the egg through the pores in its shell.

In the vacuum unit, the shell eggs are transferred, still under a negative pressure, to pressure vessel 84. Sterile gas is introduced into the vessel from one or more of the sources 86 . . . 90 under pressure; and the eggs are held in this pressurized environment for a period long enough for the selected gas or mixture of gases to infuse through the pores in the egg shell and fill the interstices of those parts of the egg within the shell.

Thereafter, the treated shell eggs may be cooled in heat exchanger 76 and packaged in unit 78. Alternatively, the pores in the egg shells may first be sealed in unit 74 to prevent unwanted exchanges between gas infused into the eggs through the pores in their shells and gases in the surrounding environs.

Figure 5:
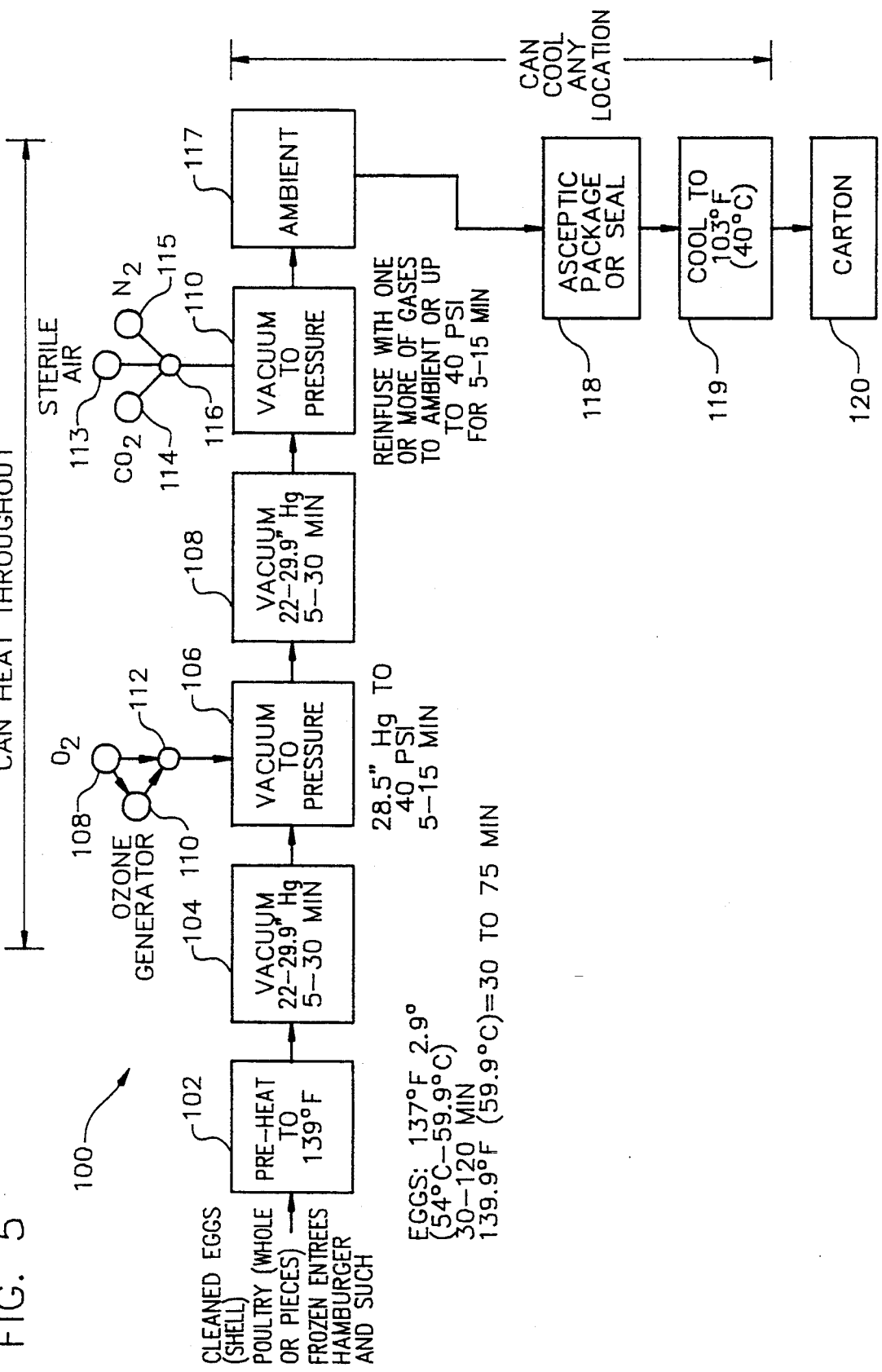

FIG. 5 depicts a system 100 which can be employed to hyperpasteurize even the most difficult-to-treat solid products—for example, full poultry carcasses. This system includes a heat exchanger 102 in which the product can be preheated in those applications of hyperpasteurization in which processing at an elevated temperature is advantageous or otherwise appropriate.

From heat exchanger 102, the product is typically transferred to a vacuum vessel 104 to remove unwanted, indigenous gases from the product.

Next, the product is transferred under a negative pressure to a previously evacuated vacuum/pressure vessel 106. That vessel is then filled with an active form of oxygen—for example, a mixture of molecular oxygen and ozone from the illustrated oxygen source 108 and ozone generator 110. A valve 112 controls the flow of the gas mixture into vessel 106.

The product is held in vessel 106 long enough for the oxygen to effect the wanted reduction in the bacterial population of the product being treated. The product is then transferred to, and held in, a vacuum vessel 108 to remove the oxygen from the product. This prevents subsequent oxidative degradation of the product, thereby improving its keeping qualities.

The product next proceeds to a previously evacuated vacuum/pressure vessel 110. Here, sterile air from a source 113, carbon dioxide from a source 114, nitrogen from a source 115, or a mixture of carbon dioxide and nitrogen is introduced into vessel 110 under pressure. The gas or gas mixture, being under pressure, reinfuses the product, preventing microbial reinfestation if sterile air is employed and achieving that result plus improving keeping qualities of the product if a sterile inert gas or inert gas mixture is used.

Flow of the selected gas or gases to vessel 110 is controlled by valve 116.

The reinfused product is preferably transferred to a separate tank 117 where the pressure on the gases is reduced to ambient. The treated product can then be packaged, preferably under aseptic conditions, in unit 118. As indicated by the legend in the block to which reference character 118 is appended in FIG. 5, unit 118 may also be employed to first perform a sealing step. As indicated above, this step may be employed to advantage in the case of shell eggs, for example, to prevent the reinfusion of the egg with unwanted gases.

In the illustrated system 100, the treated product proceeds from unit 118 to heat exchanger 119 where the product is cooled to a manageable temperature. Next, the product is transferred to packaging unit 120 where it is packaged, often to advantage in an inert gas or gas mixture.

Figure 7:
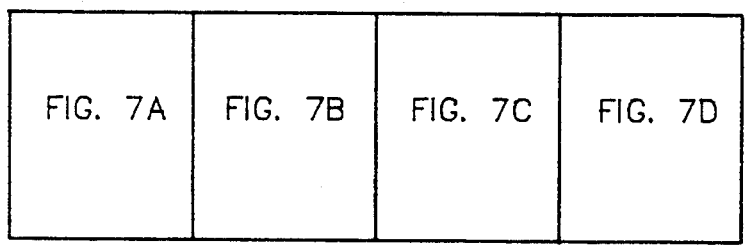
FIG. 7 shows the relationship among FIGS. 7A–7D which, taken together, constitute a schematic of a large scale system for hyperpasteurizing liquid products.
Figure 9:
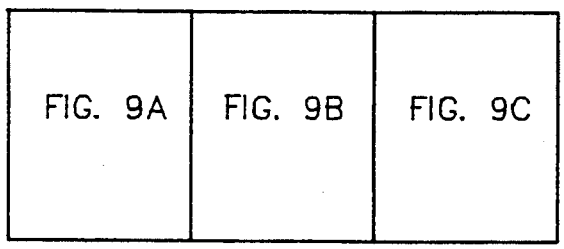
FIG. 9 shows the relationship between FIGS. 9A and 9B, and 9C which, taken together, constitute a diagram of certain hyperpasteurization steps carried out in a pressure/vacuum chamber which is part of the system shown in FIG. 8.
Figure 7B:
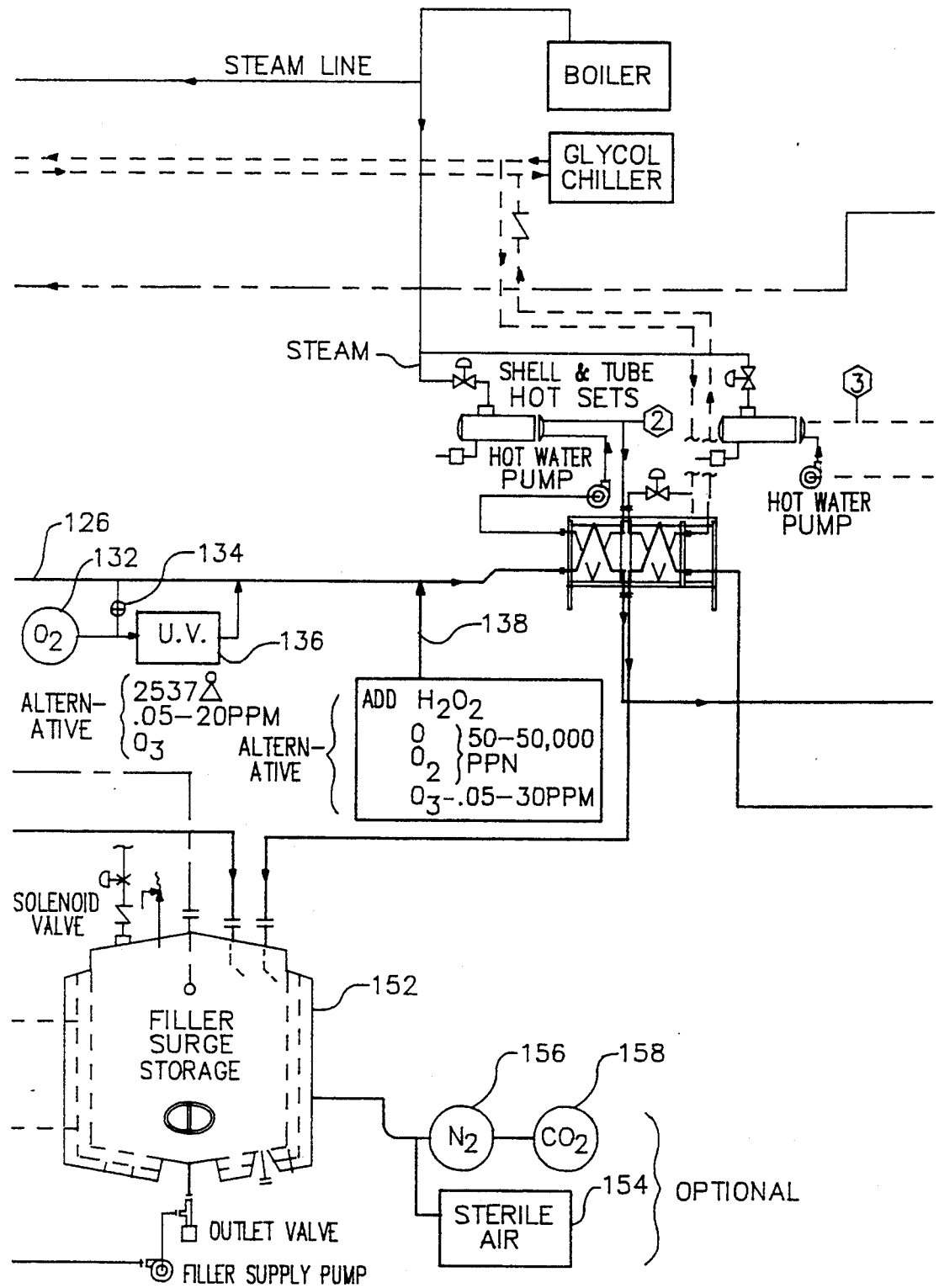
Figure 7C:
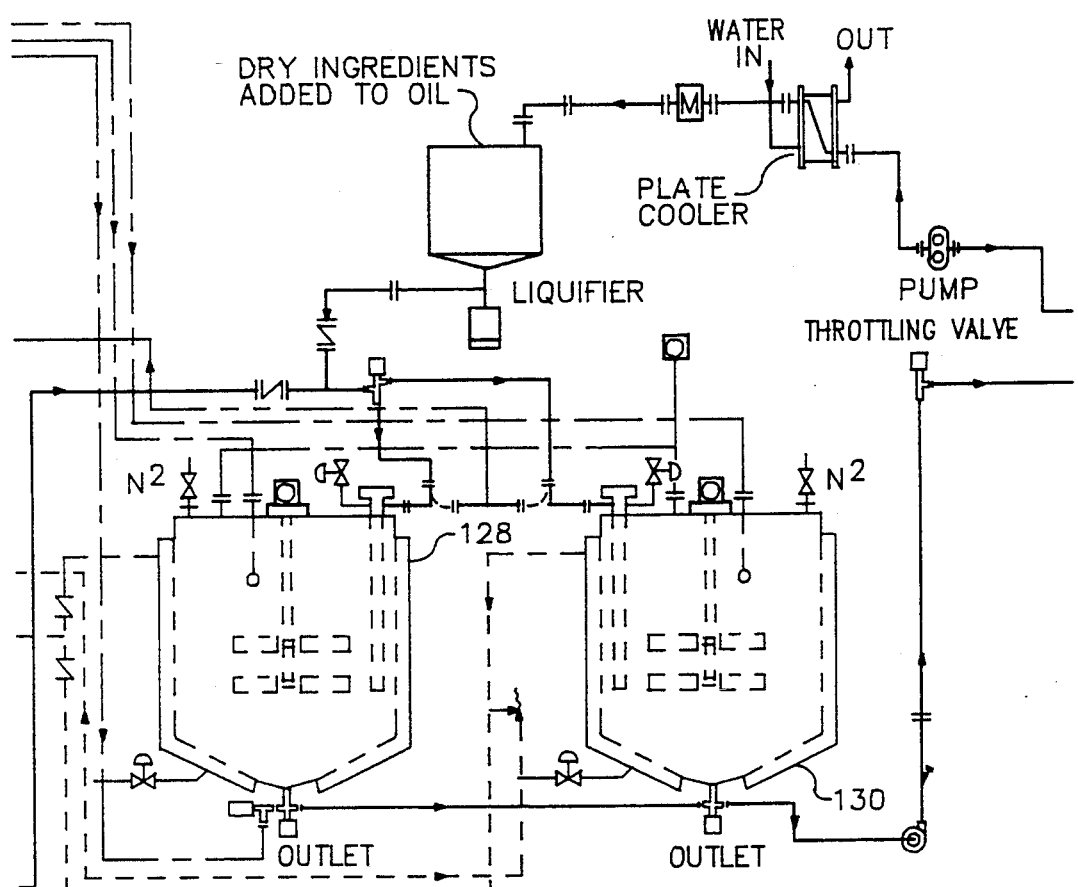
Figure 7D:
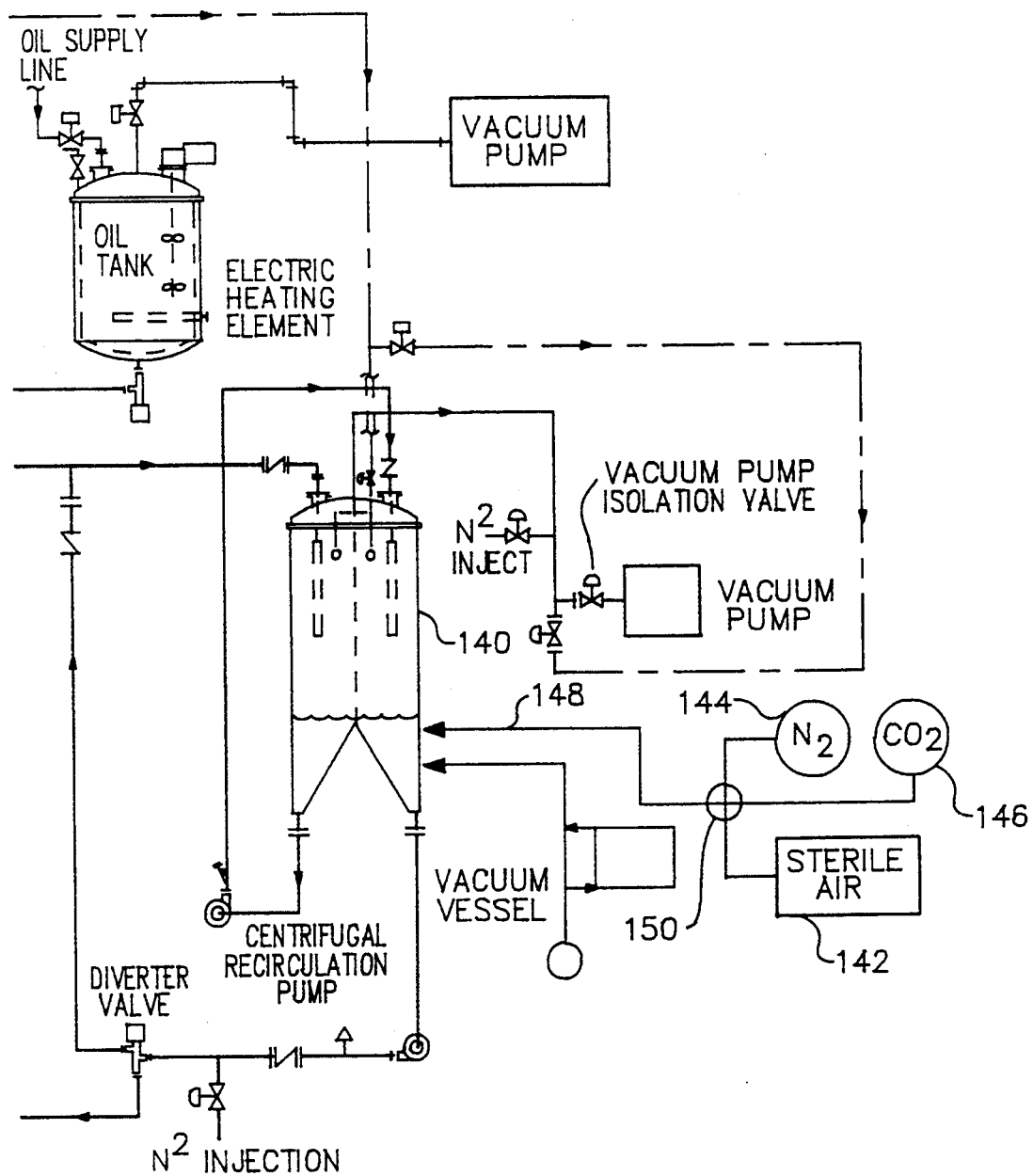

Parent applications Nos. 349,974 and 674,495 disclose processes for making novel simulated or substitute egg products and a variety of food products in which they are included such as french toast batters and a variety of mayonnaise and sauces traditionally based on eggs. A system for making and hyperpasteurizing such products is illustrated in FIG. 7 and identified by reference character 121.

To the extent that it is not employed for hyperpasteurization and ancillary processes such as packaging, system 121 is not of concern as far as the present inventions are concerned. Consequently, only those system 121 components germane to the present invention will be referred to herein.

These include a source 122, such as one of those discussed above, for introducing an active form of oxygen—the above-discussed atomic and molecular oxygen, ozone, molecular oxygen-ozone mixtures, and peroxides—into tank 124. This tank is employed to store the egg whites employed in the previously disclosed processes, and the gas or gas mixture is introduced into tank 124 to reduce the populations of harmful bacteria in the egg whites stored in that tank.

Alternatively, the selected form of oxygen may be added to the egg whites in transfer line 126 as the egg whites are pump to heated kettles 128 and 130 where they are blended with artificial egg yolks produced elsewhere in system 121 in the manner described in the parent applications.

In this case, a bottled or other oxygen source 132 is appropriate, and a valve 134 may be provided so that the oxygen can be supplied directly to the product in transfer line 26. Alternatively, as shown in FIG. 7, the oxygen can first be routed to an ultraviolet generator 136 to convert a part of the oxygen to ozone, thereby furnishing an ozone/molecular oxygen mixture to the product. Still other active forms of oxygen can be added to the product in line 126 as indicated by arrow 138.

The product made in kettles 128 and 130 is pumped from those kettles into a vacuum vessel 140 for deaeration. Once the product has been deaereated, sterile air, nitrogen, carbon dioxide, or a nitrogen/carbon dioxide mixture can be introduced into the product in vacuum vessel 140 from sources 142, 144, and 146 through a transfer line 148 to prevent recontamination of the product with microorganisms and/or oxygen-containing gases. A valve 150 in the transfer line controls the flow of the selected gas or gas mixture to the vacuum vessel.

After being cooled, the product manufactured in system 121 is transferred to a packaging unit with a surge tank 152 being employed in the transfer system between the vacuum vessel and the packaging unit to accommodate any changes that might occur in the transfer flow rate. It may prove advantageous to reintroduce sterile air into the product held in the surge tank. This can be accomplished by supplying the selected gas or gas mixture to the product in surge tank 152 from the appropriate one or ones of the illustrated sources 154, 156, and 158.

Figure 8:
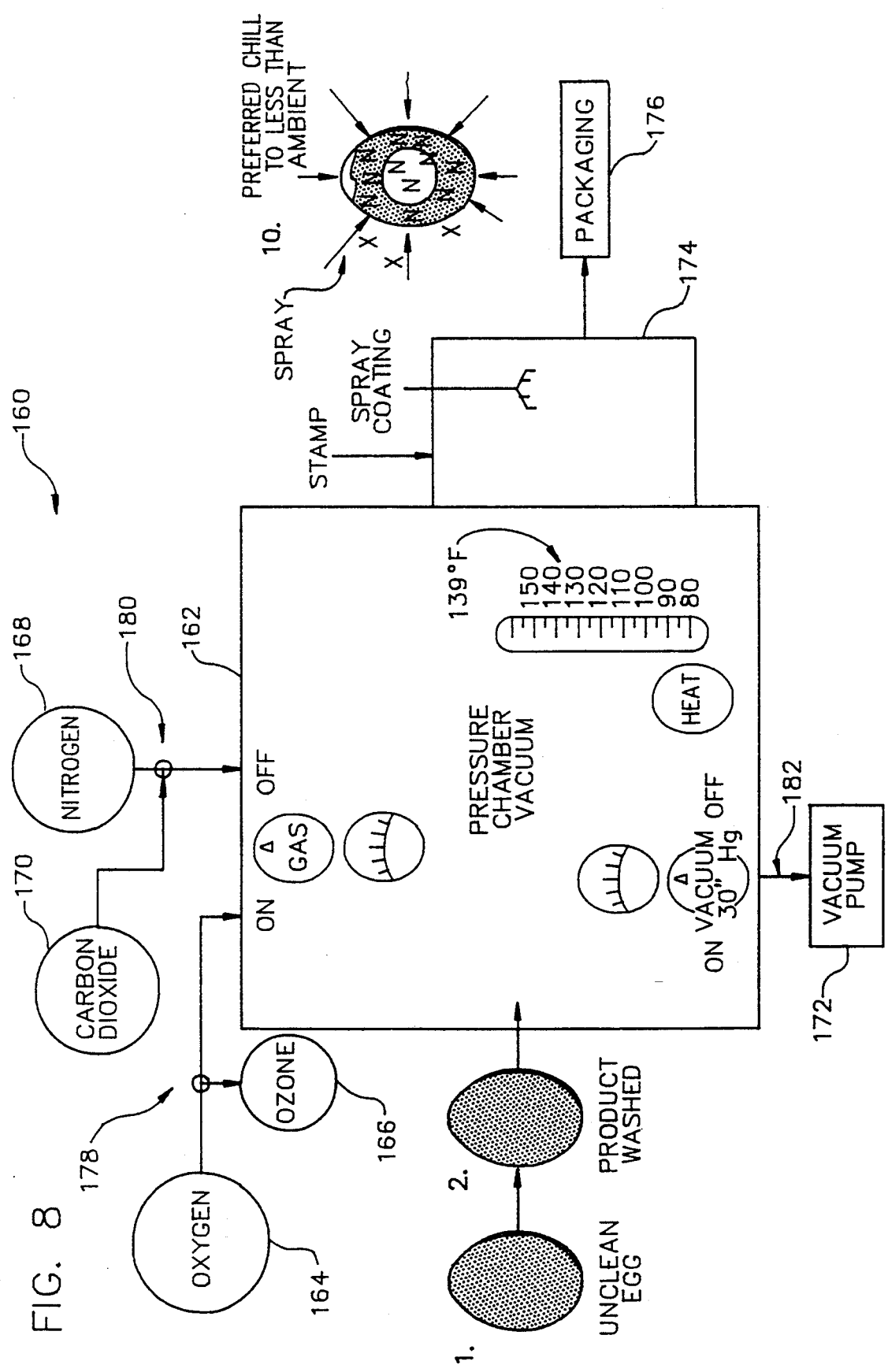
FIG. 8 is a pictorial representation of a commercial type system for hyperpasteurizing whole eggs and other solid products; certain of the hyperpasteurization steps carried out in the system are also shown in this figure.

Particularly in the case of solid products such as shell eggs, hyperpasteurization—including the steps of contacting the product with a biocidally effective form of oxygen, evacuating the oxygen from the product, and replacing the evacuated oxygen and any indigenous gases with a biocidally inactive or inert gas—can be carried out in a single pressure/vacuum chamber or vessel. A system which employs a vessel of that character is illustrated in FIG. 8 and identified by reference character 160.

In addition to pressure/vacuum chamber 162, system 160 will typically include vacuum and ozone sources 164 and 166, nitrogen and carbon dioxide sources 168 and 170, a vacuum pump 172, a stamp/spray coating unit 174, and a packaging unit 176. The oxygen and ozone sources, the nitrogen and carbon dioxide sources, and the vacuum pump 172 are connected to the interior of the pressure/vacuum chamber through transfer systems shown pictorially and identified by reference characters 174, 176, and 178.

If appropriate, as is the case with shell eggs, the product to be treated is cleaned or cleaned and disinfected before being introduced into pressure/vacuum chamber 162. Once in that chamber, the product is hyperpasteurized as discussed above—viz., by intimately contacting it with biosidedly active oxygen, subsequently removing the oxygen and indigenous gases to improve the keeping quality of the product by reducing its susceptibility to oxidative degradation, and replacing the gases evacuated from the product with an inert gas, a mixture of inert gases, or sterile oxygen to prevent recontamination of the treated product with oxygen-containing gases, unwanted microorganisms, etc.

From pressure/vacuum vessel 162, the product proceeds to unit 174. Here, if the product is shell eggs, for example, the eggs may be stamped with an indicator as discussed above so that any existent or thereafter occurring defects such as cracks in the egg shell that might permit contamination of the egg inside the shell will be made readily evident. Also, as was discussed above, a spray coating may be applied in this unit to seal the pores in the egg shell and prevent recontamination.

Subsequently, the eggs, or other products are packaged in unit 176 and then preferably refrigerated.

Many modifications may be made in those representative versions of hyperpasteurization described above without exceeding the scope of the present invention. For example, carbon monoxide may be utilized instead of a biocidally active form of oxygen to reduce microbial contamination. This gas can also be employed in the place of, or in admixture with, the inert gases identified above to prevent recontamination of the product undergoing hyperpasteurization.

As a further example, it is not necessary that a plate-type heat exchanger be used in the equipment employed for hyperpasteurization. For instance, the vacuum tank used in a typical system may itself be heated if proper agitation is provided.

The invention may be embodied in still other forms without departing from the spirit or essential characteristics of the invention. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. A method for making a shell egg safer to eat, said method comprising the steps of:
   heating said shell egg at a process temperature of greater than 129.9° F. and for a time longer than 15 minutes to reduce the microbial count in the egg while leaving the egg white substantially uncoagulated; and
   while it is at the process temperature, treating the shell egg with an infusate comprised of one or more of the following biocidally active gases to promote the reduction in the bacterial population of the egg: sterile air; filtered air; an atomic, molecular, or peroxide form of oxygen; ozone; or carbon monoxide.

2. The method of claim 1 wherein the temperature is about 139° F. and the time is more than 20 minutes but less than 18 hours.

3. The method claim 2 wherein the temperature is about 139° F. and the time is about 60 minutes.

4. The method of claim 1 in which the infusate is cholesterol oxidase.

5. The method of claim 1 in which the infusate is a mixture of air or oxygen and ozone.

6. The method claim 5 where ozone is present in the mixture in a concentration of between 0.000001 and 0.001 volume percent.

7. The method of claim 1 in which the infusate is hydrogen peroxide.

8. A method of as defined in claim 1:
   in which the infusate is biocidally active; and
   which includes the step of removing the infusate from the egg after the bacterial population of the egg has been reduced.

9. A method as defined in claim 1 in which the pores of the egg shell are sealed after the gases in the egg are replaced to thereby keep the replacement gas or gas mixture in the shell.

10. A shell egg processed by a hyperpasteurization process as defined in claim 1.

11. A method of making shell eggs safer to eat and for improving the keeping quality of such eggs, said process comprising the steps of:
    removing indigenous gases from within the shell of the egg;
    introducing into the egg a biocidally active agent in an amount effective to reduce the internal microbial count and at a temperature and for a time sufficient to reduce said internal microbial count;
    removing said agent from within the shell of the egg after the microbial count in the egg has been reduced; and
    introducing into the egg through said shell a gas which will retard spoilage of the egg.

12. A method as defined in claim 11 in which the pores of the shell are sealed after the introduction into the egg of the spoilage retarding gas.

13. A process as defined in claim 19 which includes promoting the destruction of harmful microorganisms in the egg by holding the egg at a temperature higher than 129.9° F. for a period of more than 20 minutes while the biocidally active gas is in the egg.

14. A method as defined in claim 11 in which said agent is selected from the group consisting of carbon monoxide; atomic, molecular, peroxide, and trioxygen forms of oxygen; and mixtures of two or more of the foregoing forms of oxygen.

15. A method as defined in claim 11 in which both hypobaric and hyperbaric conditions are employed.

16. A shell egg hyperpasteurized by the process defined in claim 11.

17. A method of making shell eggs safer to eat and for improving the keeping quality of such eggs, said process comprising the steps of:
    removing indigenous gases from within the shell of the egg;
    thereafter providing in the egg a biocidally active agent in an amount effective to reduce the internal microbial count and at a temperature and for a time sufficient to reduce said internal microbial count;
    removing said agent from within the shell of the egg after the microbial count in the egg has been reduced; and
    thereafter treating said egg to keep it safe to eat by inhibiting the growth of microorganisms remaining in said egg and/or recontamination of the egg by microorganisms present in the environment of the egg.

18. A method as defined in claim 17 in which the biocidally active agent comprises an active form of oxygen or a source thereof.

19. A method as defined in claim 18 in which the biocidally active agent or source comprises nascent or molecular oxygen, ozone, or a peroxide.

20. A method as defined in claim 19 in which the biocidally active agent comprises ozone, the ozone being present in said agent in a concentration ranging from 0.005 to 50 parts per million.

21. A method as defined in claim 20 in which the ozone concentration is in the range of 0.5 to 10 parts per million.

22. A method as defined in claim 19 in which the biocidally active agent is so acted upon as to generate the active form of oxygen in situ.

23. A method as defined in claim 22 in which the active form of oxygen is generated by bombarding the biocidally active agent with ultraviolet radiation.

24. A method as defined in claim 17 in which:
    the pressure on the egg is reduced to a sub-atmospheric level to effect the removal of indigenous gases from the egg; and
    the active agent is introduced into the egg by subsequently increasing the pressure on the egg to atmospheric or to a super-atmospheric level.

25. A method as defined in claim 24 in which the pressure on the egg is reduced to a negative pressure of at least 10 inches of mercury.

26. A method as defined in claim 25 in which the negative pressure is at least 24 inches of mercury.

27. A method as defined in claim 25 in which the pressure on the egg is increased in the course of providing the active treatment agent in the egg to a pressure in the range of 5 to 65 psi.

28. A method as defined in claim 27 in which the egg is held at said pressure until it reaches equilibrium.

29. A method as defined in claim 17 in which the egg is aseptically packaged to inhibit spoilage.

30. A method as defined in claim 29 in which the egg is aseptically packaged in an inert gas environment.

31. A method as defined in claim 17 in which the biocidally active agent is so formulated as to provide an active form of oxygen in the egg and in which the oxygen is removed following the reduction of the microbial population in the egg with an oxygen scavenger and/or by reducing the pressure on the egg.

32. A method as defined in claim 31 in which the active form of oxygen is removed from the egg by reducing the pressure on the egg to a negative pressure in the range of 15 to 29.9 inches of mercury.

33. A method as defined in claim 32 in which the egg is maintained at said negative pressure until the interior of the egg reaches equilibrium with the environment in which the egg is located.

34. A method as defined in claim 17 in which the egg is treated to reduce spoilage by introducing a bactericidally effective inert gas into the egg through the shell of the egg.

35. A method as defined in claim 17 in which the reduction of the microbial population in the egg is promoted by heating the egg at a selected biocidally effective temperature in the range of 129.9° to 150° F. while the biocidally active agent is present in the egg.

36. A method as defined in claim 35 in which the egg is heated for a period ranging from one minute at 150° F. up to three hours at 129.9° F.

37. A method as defined in claim 36 in which the egg is heated at a temperature in the range of 129.9° to 139° F. for a period ranging from 0.5 at 130° F. to 1.5 hours at 129.9° F.

38. A method as defined in claim 35 in which the egg is heated until the center of the egg reaches a temperature of at least 129.9° F.

39. A method as defined in claim 35 in which the active treatment agent is preheated to a temperature approximating said selected temperature before the active treatment agent is introduced into the egg.

40. A method as defined in claim 17 which includes the step of vibrating the egg to promote the removal of indigenous gases therefrom.

41. A method as defined in claim 17 in which, after the biocidally active agent has been removed from the egg, an indicator capable of warning of changes in the egg indicative of contamination is placed on the egg.

42. A method as defined in claim 41 in which the indicator comprises a resazurin dye.

43. A method as defined in claim 17 in which the egg is treated to reduce spoilage by sealing the pores in the shell of the egg.

44. A method as defined in claim 43 in which said pores are sealed with palm stearine or Vitamin E or a combination of the foregoing.

45. A method as defined in claim 17 in which the steps of removing the bactericidally effective agent from the egg and of subsequently treating the egg to inhibit spoilage are carried out at a temperature sufficiently high to promote pasteurization of the egg.

46. A method of so processing a shell egg as to improve its appearance, said method including the step of infusing into said shell egg an effective amount of an inert gas which has the ability to improve the Haugh value of the white of said egg, the shell egg being held at a temperature of about 139° F. for a time of about 60 minutes while the inert gas is infused.

47. A method of making shell eggs safer to eat and for improving the keeping quality of such eggs, said process comprising the steps removing indigenous gases from within the shell of the egg;

introducing into the egg a biocidally active agent in an amount effective to reduce the internal microbial count and at a temperature and for a time sufficient to reduce said internal microbial count;

removing said agent from within the shell of the egg after the microbial count in the egg has been reduced; and introducing into the egg through said shell a gas which will retard spoilage of the egg, said gas being selected from the group consisting of nitrogen, carbon dioxide, and mixtures of the foregoing.

48. The method of claim 47 wherein the shell pores are sealed after the infusion of the gas or gas mixture to retain infused inert gas(es) in the egg.

49. A method as defined in claim 48 which employs a sealant selected from the group consisting of saturated lipids and paraffins.

50. A method of claim 49 wherein the sealant is palm stearine.

51. A shell egg processed by a method as defined in claim 47.

* * * * *